(12) United States Patent
Kang et al.

(10) Patent No.: US 11,547,346 B2
(45) Date of Patent: Jan. 10, 2023

(54) METHOD, SERVER, AND COMPUTER PROGRAM FOR CLASSIFYING SEVERE COGNITIVE IMPAIRMENT PATIENTS BY ANALYZING EEG DATA

(71) Applicant: IMEDISYNC, INC., Seoul (KR)

(72) Inventors: Seung Wan Kang, Seoul (KR); Ukeob Park, Seoul (KR); Ju Hee Ko, Seongnam-si (KR); Namheon Kim, Paju-si (KR); Tae-gyun Jeong, Seoul (KR); Hyerin Jeong, Seoul (KR)

(73) Assignee: IMEDISYNC, INC., Seoul (KR)

( * ) Notice: Subject to any disclaimer, the term of this patent is extended or adjusted under 35 U.S.C. 154(b) by 0 days.

(21) Appl. No.: 17/680,235

(22) Filed: Feb. 24, 2022

(65) Prior Publication Data
US 2022/0287621 A1    Sep. 15, 2022

(30) Foreign Application Priority Data

Mar. 12, 2021   (KR) .......................... 10-2021-0032457

(51) Int. Cl.
*A61B 5/00* (2006.01)
*A61B 5/369* (2021.01)
(Continued)

(52) U.S. Cl.
CPC ............ *A61B 5/4088* (2013.01); *A61B 5/369* (2021.01); *A61B 5/374* (2021.01); *A61B 5/7264* (2013.01); *A61B 5/7275* (2013.01); *G16H 10/60* (2018.01); *G16H 50/20* (2018.01); *G16H 50/70* (2018.01); *A61B 2576/026* (2013.01)

(58) Field of Classification Search
None
See application file for complete search history.

(56) References Cited

FOREIGN PATENT DOCUMENTS

| JP | 2011172942 | 9/2011 |
| KR | 20180109529 A | 10/2018 |
| KR | 20180138328 | 12/2018 |

OTHER PUBLICATIONS

Durongbhan et al. A Dementia Classification Framework Using Frequency and Time-Frequency Features Based on EEG Signals IEEE Transactions on Neural Systems and Rehabilitation Engineering, vol. 27, No. 5, May 2019 (Year: 2019).*

* cited by examiner

*Primary Examiner* — Jay B Shah
(74) *Attorney, Agent, or Firm* — Fish & Richardson P.C.

(57) ABSTRACT

Provided is a method for classifying severe cognitive impairment patients by analyzing electroencephalogram (EEG) data. The method of classifying severe cognitive impairment patients by analyzing EEG data includes a brainwave collection step of collecting EEG data on a plurality of users, a first classification step of classifying the plurality of users into a severe cognitive impairment group or a non-severe cognitive impairment group by analyzing the collected EEG data, a second classification step of classifying users included in the non-severe cognitive impairment group into a normal group or an amnestic mild cognitive impairment (aMCI) group, and a third classification group of classifying users included in the normal group into a within normal limits (WNL) group or a preclinical Alzheimer's disease (AD) group and classifying users included in the aMCI group into a non-AD MCI group or a prodromal AD group.

20 Claims, 12 Drawing Sheets
(6 of 12 Drawing Sheet(s) Filed in Color)

(51) Int. Cl.
*G16H 10/60* (2018.01)
*G16H 50/70* (2018.01)
*G16H 50/20* (2018.01)
*A61B 5/374* (2021.01)

FIGURES

METHOD, SERVER, AND COMPUTER PROGRAM FOR CLASSIFYING SEVERE COGNITIVE IMPAIRMENT PATIENTS BY ANALYZING EEG DATA

CROSS-REFERENCE TO RELATED APPLICATION

This application claims priority to and the benefit of Korean Patent Application No. 10-2021-0032457, filed on Mar. 12, 2021, the disclosure of which is incorporated herein by reference in its entirety.

TECHNICAL FIELD

The present disclosure relates to a method, server, and computer program for classifying severe cognitive impairment patients by analyzing electroencephalogram (EEG) data.

BACKGROUND

Dementia refers to symptoms caused by brain diseases.

Dementia is a state of inability to perform daily activities due to a decrease in cognitive ability. When dementia progresses, thinking, behavior, and performance of daily living are affected. Doctors diagnose dementia when two or more cognitive functions (e.g., including memory, language skills, information comprehension, spatial functioning, judgment, and attention) are damaged.

People with dementia may have difficulty in solving problems and controlling their emotions and may experience personality changes. Exact symptoms experienced by people with dementia depend on which part of the brain is damaged by a disease that causes dementia. In various types of dementia, some of nerve cells in the brain stop functioning and lose connections to other cells, which leads to death. Usually, dementia progresses steadily. In other words, dementia gradually spreads to the brain, and the person's symptoms worsen over time.

In South Korea, about 290,000 or 9.5% of the elderly population over 65 are suffering from senile dementia, and 73% of them, 180,000, are seriously ill, such as habitually wandering the streets.

Since no effective medicine for dementia has been developed yet, prevention and management of dementia following early detection are most important. Until now, dementia diagnosis mainly relies on neuropsychological tests. As an auxiliary means, magnetic resonance imaging (MRI) (tests for brain deformity such as cerebral atrophy), positron emission tomography (PET) (tests for an amyloid deposition level), or the like is used, but the test cost is high. A cerebrospinal fluid test (measuring the amount of amyloid or tau protein) is an invasive method, and patients are reluctant to do the test.

To solve these problems, according to the conventional art, a dementia diagnosis platform based on electroencephalogram (EEG) data analysis was developed in which it is determined whether a patient is a patient with dementia by analyzing the patient's EEG data (e.g., analyzing whether the EEG data corresponds to that of people with dementia or that of normal people).

However, the conventional dementia diagnosis platform merely corresponds to a technology for classifying whether a patient is in a normal state or a dementia state, that is, simply and dichotomically dividing cases into the normal state and the dementia state, by analyzing EEG data. Therefore, it is possible to identify a patient who is currently suffering from dementia symptoms, but it is impossible to screen users who are in the normal state but may develop dementia.

SUMMARY

The present disclosure is directed to providing a method, a server, and a computer program for classifying severe cognitive impairment patients by analyzing electroencephalogram (EEG) data which classify a plurality of users into users in a normal state and patients with dementia by analyzing EEG data of the users and also subdivide the users' probabilities of developing dementia in the normal state in consideration of whether the users have memory impairment, the types and degrees of memory impairment, etc. not only to identify patients currently suffering from dementia but also to screen users who may develop dementia in the early stage among the users in the normal state.

Objects to be achieved by the present disclosure are not limited to that described above, and other objects which have not been described will be clearly understood by those of ordinary skill in the art from the following descriptions.

Particular implementations of the present disclosure provide a method for determining patients with severe cognitive impairment. The method includes collecting, using at least one of one or more computing devices, electroencephalogram (EEG) data on a plurality of users; analyzing, using at least one of the one or more computing devices, the collected EEG data to classify the plurality of users into a severe cognitive impairment group or a non-severe cognitive impairment group; classifying, using at least one of the one or more computing devices, users included in the non-severe cognitive impairment group into a normal group or an amnestic mild cognitive impairment (aMCI) group; classifying, using at least one of the one or more computing devices, users included in the normal group into a within normal limits (WNL) group or a preclinical Alzheimer's disease (AD) group; and classifying, using at least one of the one or more computing devices, users included in the aMCI group into a non-AD MCI group or a prodromal AD group.

In some implementations, the method can optionally include one or more of the following features. Collecting EEG data may include, for each of the plurality of users, operating a plurality of brainwave measurement channels that are disposed at a plurality of positions at each user's head, and collecting, based on the operation of the plurality of brainwave measurement channels, a plurality of pieces of unit EEG data; generating quantitative EEG (QEEG) data by (i) quantifying the plurality of collected pieces of unit EEG data and (ii) converting the plurality of quantified pieces of unit EEG data into images; and standardizing the generated QEEG data based on a preset sex-specific reference and an age-specific reference. Generating the QEEG data may include calculating, using at least one of the one or more computing devices, frequency domains for the plurality of pieces of unit EEG data based on fast-Fourier transform; rearranging, using at least one of the one or more computing devices, subset frequency domains of the calculated frequency domains based on the positions of the plurality of brainwave measurement channels, the subset frequency domains corresponding to subset pieces of unit EEG data that are measured simultaneously among the plurality of pieces of unit EEG data; and generating, using at least one of the one or more computing devices, the QEEG data in a form of a symmetrical image by accumulating the rearranged subset pieces of unit EEG data over time. Analyzing the collected EEG data may include performing, using at least one of the one or more computing devices, image analysis of the generated QEEG data using a first classification model; calculating, using at least one of the one or more computing devices and based on the image analysis, a severe cognitive impairment probability and a non-severe cognitive impairment probability of each of the plurality of users; and classifying, using at least one of the one or more computing devices and based on the calculated severe cognitive impairment probabilities and the calculated non-severe cognitive impairment probabilities, the plurality of users into the severe cognitive impairment group or the non-severe cognitive impairment group. Classifying the users included in the non-severe cognitive impairment group into the normal group or the aMCI group, may include classifying first users with memory impairment into the aMCI group, the first users being selected from the users included in the non-severe cognitive impairment group; and classifying second users into the normal group based on a second classification model, the second users being not classified into the aMCI group. Classifying the users included in the normal group into the WNL group or the preclinical AD group, may include generating an optimized classification model for user classification, the optimized classification model including a third classification model and a fourth classification model; classifying third users without subjective cognitive decline (SCD) into the WNL group, the third user being selected from the users included in the normal group; classifying fourth users with SCD into the preclinical AD group based on the third classification model; classifying fifth users with retrieval failure into the non-AD MCI group, the fifth users being selected from the users included in the aMCI group; and classifying sixth users with encoding failure into the prodromal AD group based on the fourth classification model. Generating the optimized classification model may include generating a plurality of multidimensional models by: (i) deriving a plurality of feature values by analyzing the plurality of pieces of EEG data collected from each of the plurality of users, (ii) randomly and repeatedly selecting a preset number of feature values from the plurality of feature values, (iii) generating, based on the selection of the preset number of feature values, a plurality of feature value combinations, and (iv) generating the plurality of multidimensional models based on each of the plurality of feature value combinations; calculating an accuracy of each of the plurality of multidimensional models; selecting N multidimensional models in decreasing order of accuracy; counting a number of feature values included in each of the selected N multidimensional models; selecting M feature values in decreasing order of count value; and generating the optimized classification model including the selected M feature values. The method may include scoring, based on (i) classifying the plurality of users into the severe cognitive impairment group or the non-severe cognitive impairment group, (ii) classifying the users included in the non-severe cognitive impairment group into the normal group or the aMCI group, and (iii) classifying the users included in the normal group into the WNL group or the preclinical AD group, severe cognitive impairment levels of users included in each of the WNL group, the preclinical AD group, the non-AD MCI group, the prodromal AD group, and the severe cognitive impairment group. Scoring the severe cognitive impairment levels of the users may include: scoring 0 to 50 to the users included in the WNL group based on the severe cognitive impairment levels; scoring 50 to 60 to the users included in the preclinical AD group based on the severe cognitive impairment levels; scoring 60 to 70 to the users included in the non-AD MCI group based on the severe cognitive impairment levels; scoring 70 to 85 to the users included in the prodromal AD group based on the severe cognitive impairment levels; and scoring 85 to 100 to the users included in the severe cognitive impairment group based on the severe cognitive impairment levels.

Particular implementations of the present disclosure provide a server for classifying severe cognitive impairment patients by analyzing electroencephalogram (EEG) data. The server may include a processor; and a memory storing instructions that, when executed by the processor, cause the server to perform operations comprising: collecting electroencephalogram (EEG) data on a plurality of users; analyzing the collected EEG data to classify the plurality of users into a severe cognitive impairment group or a non-severe cognitive impairment group; classifying users included in the non-severe cognitive impairment group into a normal group or an amnestic mild cognitive impairment (aMCI) group; classifying users included in the normal group into a within normal limits (WNL) group or a preclinical Alzheimer's disease (AD) group; and classifying users included in the aMCI group into a non-AD MCI group or a prodromal AD group.

In some implementations, the server can optionally include one or more of the following features. Collecting EEG data may include, for each of the plurality of users, operating a plurality of brainwave measurement channels that are disposed at a plurality of positions at each user's head, and collecting, based on the operation of the plurality of brainwave measurement channels, a plurality of pieces of unit EEG data; generating quantitative EEG (QEEG) data by quantifying the plurality of collected pieces of unit EEG data and converting the plurality of quantified pieces of unit EEG data into images; and standardizing the generated QEEG data based on a preset sex-specific reference and an age-specific reference. Generating the QEEG data may include: calculating frequency domains for the plurality of pieces of unit EEG data based on fast-Fourier transform; rearranging subset frequency domains of the calculated frequency domains based on the positions of the plurality of brainwave measurement channels, the subset frequency domains corresponding to subset pieces of unit EEG data that are measured simultaneously among the plurality of pieces of unit EEG data; and generating the QEEG data in a form of a symmetrical image by accumulating the rearranged subset pieces of unit EEG data over time.

Particular implementations of the present disclosure provide a non-transitory computer-readable medium having stored therein a computer program for causing a computing device to execute operations including collecting electroencephalogram (EEG) data on a plurality of users; analyzing the collected EEG data to classify the plurality of users into a severe cognitive impairment group or a non-severe cognitive impairment group; classifying users included in the non-severe cognitive impairment group into a normal group or an amnestic mild cognitive impairment (aMCI) group; classifying users included in the normal group into a within normal limits (WNL) group or a preclinical Alzheimer's disease (AD) group; and classifying users included in the aMCI group into a non-AD MCI group or a prodromal AD group.

In some implementations, the operations can optionally include one or more of the following features. Collecting EEG data on a plurality of users may include, for each of the plurality of users, operating a plurality of brainwave measurement channels that are disposed at a plurality of positions at each user's head, and collecting, based on the operation of the plurality of brainwave measurement channels, a plurality of pieces of unit EEG data; generating quantitative EEG (QEEG) data by quantifying the plurality of collected pieces of unit EEG data and converting the plurality of quantified pieces of unit EEG data into images; and standardizing the generated QEEG data based on a preset sex-specific reference and an age-specific reference. Generating the QEEG data may include calculating frequency domains for the plurality of pieces of unit EEG data based on fast-Fourier transform; rearranging subset frequency domains of the calculated frequency domains based on the positions of the plurality of brainwave measurement channels, the subset frequency domains corresponding to subset pieces of unit EEG data that are measured simultaneously among the plurality of pieces of unit EEG data; and generating the QEEG data in a form of a symmetrical image by accumulating the rearranged subset pieces of unit EEG data over time.

One aspect of the present disclosure provides a method of classifying severe cognitive impairment patients by analyzing electroencephalogram (EEG) data, the method performed by a computing device and including a brainwave collection step of collecting EEG data on a plurality of users, a first classification step of classifying the plurality of users into a severe cognitive impairment group or a non-severe cognitive impairment group by analyzing the collected EEG data, a second classification step of classifying users included in the non-severe cognitive impairment group into a normal group or an amnestic mild cognitive impairment (aMCI) group, and a third classification group of classifying users included in the normal group into a within normal limits (WNL) group or a preclinical Alzheimer's disease (AD) group and classifying users included in the aMCI group into a non-AD MCI group or a prodromal AD group.

The brainwave collection step may include collecting a plurality of pieces of unit EEG data through a plurality of brainwave measurement channels attached to different positions on a first user's head, generating quantitative EEG (QEEG) data by quantifying the collected plurality of pieces of unit EEG data and turning the quantified plurality of pieces of unit EEG data into images, and standardizing the generated QEEG data on the basis of preset sex- and age-specific references.

The generating of the QEEG data may include calculating frequency domains for the measured plurality of pieces of unit EEG data on the basis of fast-Fourier transform, rearranging the frequency domains corresponding to a plurality of pieces of unit EEG data measured at the same point in time among the measured plurality of pieces of unit EEG data according to positions of the plurality of brainwave measurement channels on the basis of the calculated frequency domains, and generating QEEG data in the form of a symmetrical image by cumulating the rearranged plurality of pieces of unit EEG data over time.

The first classification step may include calculating a severe cognitive impairment probability and a non-severe cognitive impairment probability of each of the plurality of users by performing image analysis of the generated QEEG data using a first classification model and classifying the plurality of users into the severe cognitive impairment group or the non-severe cognitive impairment group using the calculated severe cognitive impairment probabilities and the calculated non-severe cognitive impairment probabilities.

The second classification step may include classifying users with memory impairment into the aMCI group among the users included in the non-severe cognitive impairment group and classifying users, who are not classified into the aMCI group, into the normal group using a second classification model.

The third classification step may include generating an optimized classification model, which includes a third classification model and a fourth classification model, for user classification, classifying users without subjective cognitive decline (SCD) among the users included in the normal group into the WNL group and classifying users with SCD into the preclinical AD group using the third classification model, and classifying users with retrieval failure among the users included in the aMCI group into the non-AD MCI group and classifying users with encoding failure into the prodromal AD group using the fourth classification model.

The generating of the optimized classification model may include generating a plurality of different feature value combinations by randomly and repeatedly selecting a preset number of feature values from among a plurality of feature values derived by analyzing the plurality of pieces of EEG data collected from each of the plurality of users and generating a plurality of multidimensional models using each of the generated plurality of feature value combinations, calculating an accuracy of each of the generated plurality of multidimensional models, and selecting top N multidimensional models in decreasing order of accuracy, counting the number of each of feature values included in each of the N selected multidimensional models, selecting M feature values in decreasing order of count value, and generating the optimized classification model including the selected M feature values.

The method may further include scoring severe cognitive impairment levels of users included in each of the WNL group, the preclinical AD group, the non-AD MCI group, the prodromal AD group, and the severe cognitive impairment group using classification results of the first classification step, classification results of the second classification step, and classification results of the third classification step.

The scoring of the severe cognitive impairment levels of the users may include giving scores of 0 to 50 to the users included in the WNL group according to the severe cognitive impairment levels, giving scores of 50 to 60 to the users included in the preclinical AD group according to the severe cognitive impairment levels, giving scores of 60 to 70 to the users included in the non-AD MCI group according to the severe cognitive impairment levels, giving scores of 70 to 85 to the users included in the prodromal AD group according to the severe cognitive impairment levels, and giving scores of 85 to 100 to the users included in the severe cognitive impairment group according to the severe cognitive impairment levels.

Another aspect of the present disclosure provides a server for classifying severe cognitive impairment patients by analyzing EEG data, the server including a processor, a network interface, a memory, and a computer program loaded to the memory and executed by the processor. The computer program includes a brainwave collection instruction for collecting EEG data of a plurality of users, a first classification instruction for classifying the plurality of users into a severe cognitive impairment group or a non-severe cognitive impairment group by analyzing the collected EEG data, a second classification instruction for classifying users included in the non-severe cognitive impairment group into a normal group or an aMCI group, and a third classification instruction for classifying users included in the normal group into a WNL group or a preclinical AD group and classifying users included in the aMCI group into a non-AD MCI group or a prodromal AD group.

Another aspect of the present disclosure provides a computer program recorded on a computer-readable recording medium which is combined with a computing device to perform a brainwave collection step of collecting EEG data of a plurality of users, a first classification step of classifying the plurality of users into a severe cognitive impairment group or a non-severe cognitive impairment group by analyzing the collected EEG data, a second classification step of classifying users included in the non-severe cognitive impairment group into a normal group or an aMCI group, and a third classification step of classifying users included in the normal group into a WNL group or a preclinical AD group and classifying users included in the aMCI group into a non-AD MCI group or a prodromal AD group.

Other details of the present disclosure are included in the detailed description and the drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features and advantages of the present disclosure will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
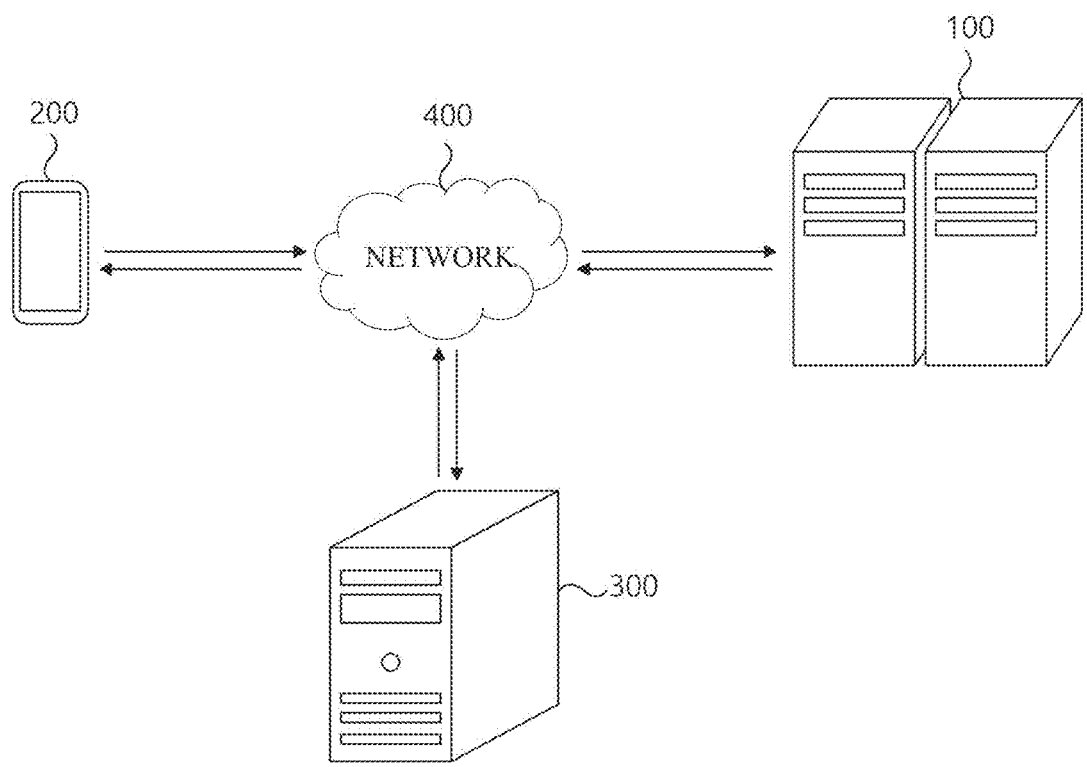
FIG. 1 is a diagram illustrating a system for classifying severe cognitive impairment patients by analyzing electroencephalogram (EEG) data according to an embodiment of the present disclosure.

Advantages and features of the present disclosure and a method of achieving them will become apparent from embodiments which will be described in detail below with reference to the accompanying drawings. However, the present disclosure is not limited to the embodiments disclosed below and may be implemented in various forms. The embodiments are provided to make the disclosure of the present disclosure complete and fully inform those of ordinary skill in the art to which the present disclosure pertains of the scope of the present disclosure. The present disclosure is only defined by the scope of the claims.

Terminology used herein is for the purpose of describing embodiments only and is not intended to be limiting the present disclosure. As used herein, the singular forms include the plural forms as well unless the context clearly indicates otherwise. The terms "comprises" and/or "comprising" do not preclude the presence or addition of one or more elements other than stated elements. Throughout the specification, like numbers refer to like elements, and "and/or" includes any one or all possible combinations of stated elements. Although "first," "second," etc. are used to describe various elements, the elements are not limited by the terms. These terms are used to distinguish one element from other elements. Accordingly, it is apparent that a first element described below may be a second element without departing from the technical spirit of the present disclosure.

Unless otherwise defined, all terms (including technical and scientific terms) may have meanings generally understood by those of ordinary skill in the art to which the present disclosure pertains. Also, unless defined otherwise, all terms defined in generally used dictionaries are not to be ideally or excessively interpreted.

The term "unit" or "module" used herein means a software or hardware element, such as a field-programmable gate array (FPGA) and an application-specific integrated circuit (ASIC), and a "unit" or "module" performs certain roles. However, a "unit" or "module" is not limited to software or hardware. A "unit" or "module" may be configured to be in an addressable storage medium or may be configured to run on one or more processors. Therefore, as an example, a "unit" or "module" may include elements, such as software elements, object-oriented software elements, class elements, and task elements, as well as processors, functions, attributes, procedures, subroutines, segments of program code, drivers, firmware, micro-code, circuits, data, databases, data structures, tables, arrays, and variables. Functions provided in elements and "units" or "modules" may be combined into a smaller number of elements and "units" or "modules" or subdivided into additional elements and "units" or "modules."

Spatially relative terms, such as "below," "beneath," "lower," "above," "upper," etc., as illustrated in the drawings, may be used to facilitate the description of relationships between an element and other elements. The spatially relative terms should be understood as terms that include different directions of the element in use or operation in addition to the direction illustrated in the drawings. For example, when an element illustrated in a drawing is reversed, another element described to be "below" or "beneath" the element may be "above" the element. Accordingly, the exemplary term "below" may include both upward and downward directions. An element may be directed in another direction, and the spatially relative terms may be interpreted accordingly.

In the specification, a computer refers to any type of hardware device including at least one processor and may be understood as encompassing software elements operating in a corresponding hardware device according to embodiments. For example, a computer may be understood as encompassing but not limited to all of a smartphone, a tablet personal computer (PC), a desktop, a laptop, and a user client and applications running on each of the devices.

Hereinafter, embodiments of the present disclosure will be described in detail with reference to the accompanying drawings.

Each step described herein is described as being performed by a computer, but the subject of each step is not limited thereto, and at least some of the steps may be performed in different devices according to embodiments.

In this specification, it is described that a plurality of users are classified on the basis of severe cognitive impairment (e.g., Alzheimer's disease dementia (ADD)), but the application is not limited thereto. In the same or a similar manner, the present disclosure can be applied to various diseases that can be classified by analyzing users' biometric data including electroencephalogram (EEG) data.

FIG. 1 is a diagram illustrating a system for classifying severe cognitive impairment patients by analyzing EEG data according to an embodiment of the present disclosure.

Referring to FIG. 1, the system for classifying severe cognitive impairment patients by analyzing EEG data according to the embodiment of the present disclosure may include a severe cognitive impairment patient classification server 100, a user terminal 200, and an external server 300.

The system for classifying severe cognitive impairment patients by analyzing EEG data shown in FIG. 1 is in accordance with the embodiment. The components are not limited to the embodiment shown in FIG. 1, and some of the components may be changed or removed or some other components may be added as necessary.

In the embodiment, the severe cognitive impairment patient classification server 100 may collect EEG data of a plurality of users and classify each of the plurality of users into any one of a severe cognitive impairment group, a within normal limits (WNL) group, a preclinical Alzheimer's disease (AD) group, a non-AD mild cognitive impairment (MCI) group, and a prodromal AD group by analyzing the collected EEG data. However, the classification is not limited thereto.

In various embodiments, the severe cognitive impairment patient classification server 100 may determine whether a user is a severe cognitive impairment patient by analyzing the user's EEG data according to the user's request and provide a result report (e.g., FIGS. 11 and 12) including the determination results (e.g., information on a group to which the user belongs and information about whether the user has dementia or information on the probability (score) of developing dementia. For example, the severe cognitive impairment patient classification server 100 may be connected to the user terminal 200 and a brainwave measurement device through a network 400 and may generate and provide a result report by collecting and analyzing EEG data from the brainwave measurement device in response to a diagnosis request obtained from the user terminal 200. An example of the brainwave measurement device is described in U.S. patent application Ser. No. 17/668,060, titled EEG Measuring Device, the disclosure of which is incorporated by reference herein in its entirety.

The network 400 may refer to a connection structure in which information can be exchanged between nodes such as a plurality of terminals and servers. For example, the network 400 may include a local area network (LAN), a wide area network (WAN), the Internet (the world wide web (WWW)), a wired or wireless data communication network, the public switched telephone network (PSTN), a wired or wireless television communication network, and the like.

The wireless data communication network may include, but is not limited to, a third generation (3G) network, a fourth generation (4G) network, a fifth generation (5G) network, a third generation partnership project (3GPP) network, a fifth generation partnership project (5GPP) network, a Long Term Evolution (LTE) network, a worldwide interoperability for microwave access (WiMAX) network, a Wi-Fi network, the Internet, a LAN, a wireless LAN, a WAN, a personal area network (PAN), a radio frequency (RF) network, a Bluetooth network, a near-field communication (NFC) network, a satellite broadcasting network, an analog broadcast network, a digital multimedia broadcasting (DMB) network, etc.

In the embodiment, the user terminal 200 may be connected to the severe cognitive impairment patient classification server 100 through the network 400. The user terminal 200 may request execution of a severe cognitive impairment patient classification process based on EEG data analysis through a user interface (UI) provided by the severe cognitive impairment patient classification server 100 and receive a result report including information on the group to which the user belongs and information about whether the user has dementia or information on the probability (score) of developing dementia in response to the request.

In various embodiments, the user terminal 200 is a wireless communication device which ensures portability and mobility and may include, but is not limited to, any type of handheld wireless communication device such as a navigation device, a personal communication system (PCS), a global system for mobile communications (GSM), a personal digital cellular (PDC) device, a personal handyphone system (PHS) device, a personal digital assistant (PDA), an international mobile telecommunication (IMT)-2000 device, a code division multiple access (CDMA)-2000 device, a wideband CDMA (W-CDMA) device, a wireless broadband Internet (WiBro) device, a smartphone, a smartpad, a tablet PC, etc.

In the embodiment, the external server 300 may be connected to the severe cognitive impairment patient classification server 100 through the network 400 and may store and manage various pieces of information/data required for the severe cognitive impairment patient classification server 100 to perform a severe cognitive impairment patient classification process based on EEG data analysis or store and manage various pieces of information/data generated by performing the severe cognitive impairment patient classification process based on EEG data analysis. For example, the external server 300 may be a storage server that is separately provided outside the severe cognitive impairment patient classification server 100 but is not limited thereto. A hardware configuration of the severe cognitive impairment patient classification server 100 will be described below with reference to FIG. 2.

Figure 2:
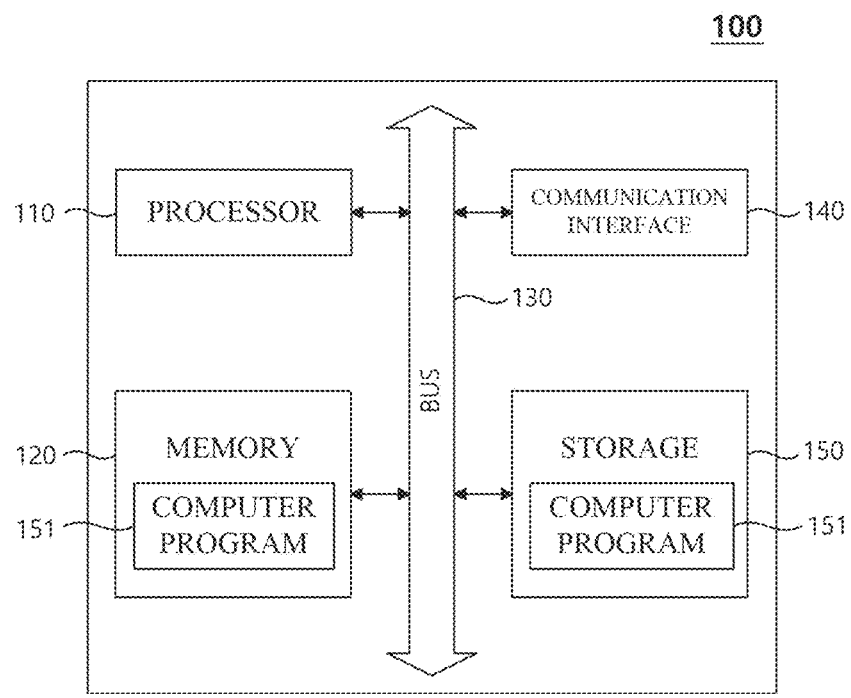
FIG. 2 is a diagram illustrating a hardware configuration of a server for classifying severe cognitive impairment patients by analyzing EEG data according to another embodiment of the present disclosure.

FIG. 2 is a diagram illustrating a hardware configuration of a server for classifying severe cognitive impairment patients by analyzing EEG data according to another embodiment of the present disclosure.

Referring to FIG. 2, the severe cognitive impairment patient classification server 100 (hereinafter, "the server 100") according to the embodiment of the present disclosure may include at least one processor 110, a memory 120 to which a computer program 151 executed by the processor 110 is loaded, a bus 130, a communication interface 140, and a storage 150 storing the computer program 151. In FIG. 2, only components related to embodiments of the present disclosure are shown. Accordingly, those of ordinary skill in the art to which the present disclosure pertains may appreciate that other general-purpose components may be included in addition to the components shown in FIG. 2.

The processor 110 controls overall operations of each element of the server 100. The processor 110 may include a central processing unit (CPU), a micro-processor unit (MPU), a micro-controller unit (MCU), a graphic processing unit (GPU), or any form of processor well known in the technical field of the present disclosure.

The processor 110 may perform computation for at least one application or program for performing methods according to embodiments of the present disclosure, and the server 100 may include at least one processor.

In various embodiments, the processor 110 may further include a random access memory (RAM) and read-only memory (ROM) which temporarily and/or permanently store signals (or data) processed in the processor 110. The processor 110 may be implemented in the form of a system on chip (SoC) including at least one of a graphics processing unit, a RAM, and a ROM.

The memory 120 stores various pieces of data, various commands, and/or various pieces of information. The memory 120 may load the computer program 151 from the storage 150 to perform methods/operations according to various embodiments of the present disclosure. When the computer program 151 is loaded to the memory 120, the processor 110 may perform the methods/operations by executing one or more instructions constituting the computer program 151. The memory 120 may be implemented as a volatile memory, such as a RAM, but the technical scope of the present disclosure is not limited thereto.

The bus 130 provides a communication function between components of the server 100. The bus 130 may be implemented in various forms of buses such as an address bus, a data bus, and a control bus.

The communication interface 140 supports wired or wireless Internet communication of the server 100. Also, the communication interface 140 may support various communication methods other than Internet communication. To this end, the communication interface 140 may include communication modules well known in the technical field of the present disclosure. In some embodiments, the communication interface 140 may be omitted.

The storage 150 may non-temporarily store the computer program 151. When a severe cognitive impairment patient classification process based on EEG data analysis is performed by the server 100, the storage 150 may store various pieces of information required for providing the severe cognitive impairment patient classification process based on EEG data analysis.

The storage 150 may include a non-volatile memory, such as a ROM, an erasable programmable ROM (EPROM), an electrically erasable programmable ROM (EEPROM), and a flash memory, a hard disk, a detachable disk, or any form of computer-readable recording medium well known in the technical field to which the present disclosure pertains.

The computer program 151 may include one or more instructions that cause the processor 110 to perform the methods/operations according to various embodiments of the present disclosure when loaded to the memory 120. In other words, the processor 110 may perform the methods/operations according to various embodiments by executing the one or more instructions.

In the embodiment, the computer program 151 may include one or more instructions for performing a method of classifying cognitive impairment patients by analyzing EEG data, and the method includes a brainwave collection step of collecting EEG data of a plurality of users, a first classification step of classifying the plurality of users into a severe cognitive impairment group or a non-severe cognitive impairment group by analyzing the collected EEG data, a second classification step of classifying users included in the non-severe cognitive impairment group into a normal group or an amnestic mild cognitive impairment (aMCI) group, and a third classification group of classifying users included in the normal group into a within normal limits (WNL) group or a preclinical Alzheimer's disease (AD) group and classifying users included in the aMCI group into a non-AD MCI group or a prodromal AD group.

Steps of a method or algorithm described regarding an embodiment of the present disclosure may be directly implemented as hardware, implemented as a software module executed by hardware, or implemented as a combination of the hardware and software module. The software module may be on a RAM, a ROM, an EPROM, an EEPROM, a flash memory, a hard disk, a detachable disk, a compact disc (CD)-ROM, or any type of computer-readable recording medium well known in the technical field to which the present disclosure pertains.

Components of the present disclosure may be implemented as a program (or an application) and stored in a medium to be executed in combination with a computer which is hardware. Components of the present disclosure may be implemented with software programming or software modules. Similarly, embodiments may be implemented with a programming or scripting language, such as C, C++, Java, or assembler, to include various algorithms implemented as data structures, processes, routines, or combinations of other programming elements. Functional aspects may be implemented by an algorithm that is executed in one or more processor. A process performed by the server 100 to classify severe cognitive impairment patients by analyzing EEG data will be described below with reference to FIGS. 3 to 12.

Figure 3:
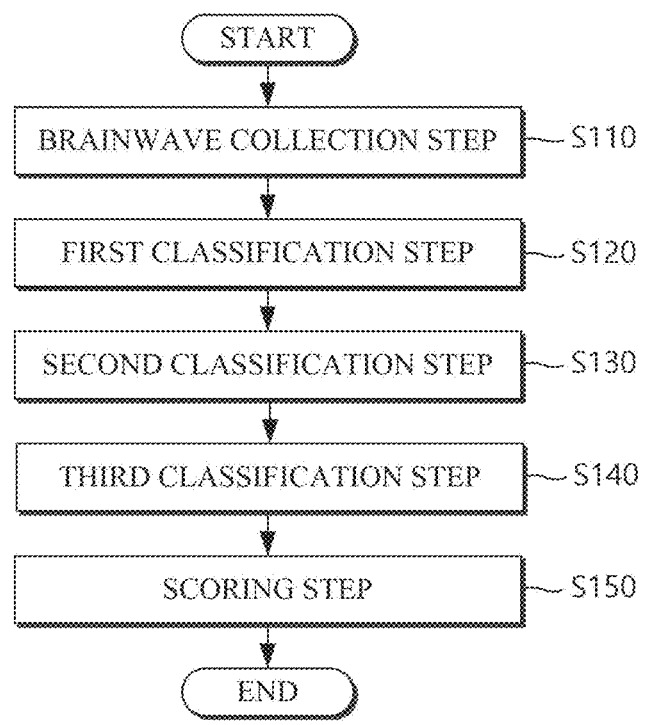
FIG. 3 is a flowchart illustrating a method of classifying severe cognitive impairment patients by analyzing EEG data according to still another embodiment of the present disclosure.
Figure 4:
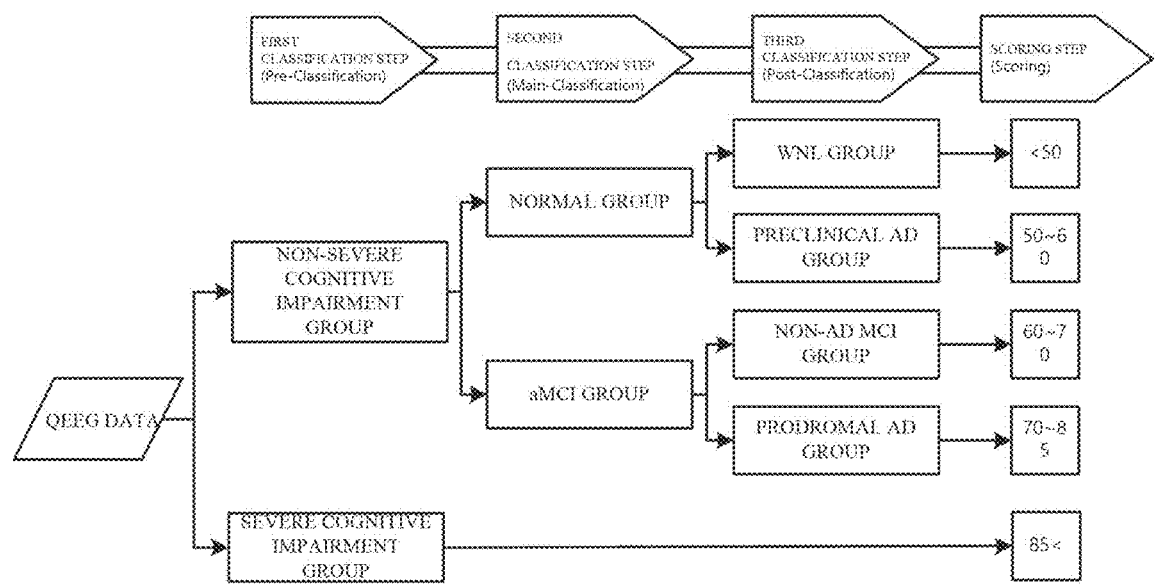
FIG. 4 is a diagram illustrating a process of classifying and scoring users according to the method of classifying severe cognitive impairment patients by analyzing EEG data in various embodiments.

FIG. 3 is a flowchart illustrating a method of classifying severe cognitive impairment patients by analyzing EEG data according to still another embodiment of the present disclosure, and FIG. 4 is a diagram illustrating a process of classifying and scoring users according to the method of classifying severe cognitive impairment patients by analyzing EEG data in various embodiments.

Referring to FIGS. 3 and 4, in step S110, the server 100 may perform a brainwave collection operation of collecting EEG data of a plurality of users. For example, the server 100 may collect EEG data of the plurality of users measured in real time by a brainwave measurement device. However, the brainwave collection operation is not limited thereto, and the server 100 may receive previously stored EEG data of the plurality of users from the external server 300.

The EEG data may be a plurality of pieces of unit EEG data (e.g., independent brainwave signals separately measured through channels) measured through a brainwave measurement device including a plurality of brainwave measurement channels (e.g., a total of 19 channels (e.g., Fp1, Fp2, F3, F4, C3, C4, P3, P4, O1, O2, F7, F8, T3, T4, T5, T6, Fz, Cz, and Pz)) attached at different positions on a user's head (scalp).

In various embodiments, the server 100 may collect not only EEG data measured in a normal state in which each the plurality of users does not take any action but also EEG data measured during a process of performing various tests (e.g., a verbal fluency test, a Boston naming test, a mini mental state examination, a word list memory test, a constructional behavior test, a word list recall test, a word list recognition test, a constructional recall test, and a path making test A/B).

In various embodiments, the server 100 may generate a plurality of pieces of quantitative EEG (QEEG) data by processing each piece of the EEG data collected from the plurality of users. This will be described below with reference to FIGS. 5 and 6.

Figure 5:
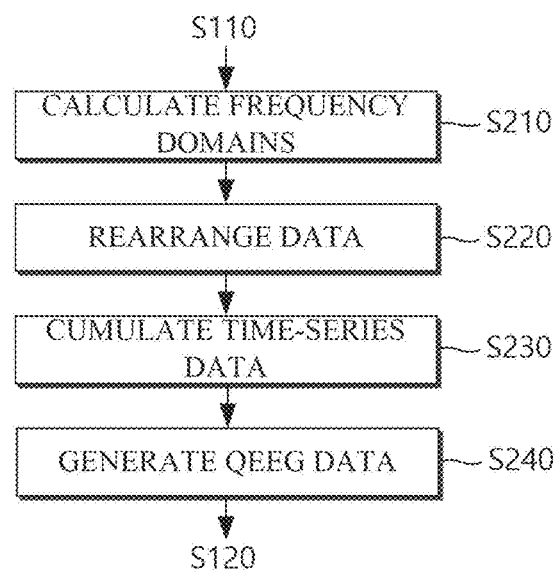
FIGS. 5, 6A and 6B are diagrams illustrating a method of generating quantitative EEG (QEEG) data in various embodiments.

FIGS. 5 and 6 are diagrams illustrating a method of generating QEEG data in various embodiments.

Referring to FIGS. 5 and 6, in step S210, the server 100 may calculate frequency domains for a plurality of pieces of unit EEG data collected through a plurality of brainwave measurement channels attached to different positions on a first user's head.

In various embodiments, the server 100 may generate at least one spectrogram (e.g., FIG. 6A) by performing a frequency conversion on each of the plurality of pieces of unit EEG data on the basis of a predetermined range of frequency.

The spectrogram is for identifying sounds or waves in a visual manner and may be related to an image showing characteristics of a waveform and a spectrum in combination. The spectrogram may represent a difference in amplitude with a difference in print density or display color along a time axis and a frequency axis. However, the spectrogram is not limited thereto.

Also, the predetermined range of frequency may be from 1 Hz to 45 Hz but is not limited thereto.

In various embodiments, when a time for which EEG data is measured is less than a preset time (e.g., four seconds), the server 100 may adjust the size of the spectrogram to a square matrix. For example, the server 100 may calculate a relative power (a relative intensity in a corresponding time band) of each spectrogram configured in a square matrix on the basis of a time axis and perform scaling between −1 and 1 on the basis of the largest value in each matrix to generate one or more spectrograms. However, a method of adjusting a spectrogram is not limited thereto.

In various embodiments, the server may calculate a frequency domain on the basis of fast-Fourier transform, specifically, using a superlet technique to efficiently represent a change over time depending on frequency. However, a frequency domain calculation method is not limited thereto, and various frequency domain calculation methods (e.g., wavelet transform) may be applied.

In step S220, the server 100 may generate a plurality of pieces of image subdata (e.g., FIG. 6B) by rearranging the frequency domains, which correspond to a plurality of pieces of unit EEG data measured through the brainwave measurement channels at the same point in time among the plurality of pieces of unit EEG data, according to positions of the plurality of brainwave measurement channels.

For example, the server 100 may generate image subdata by rearranging a plurality of pieces of unit EEG data, which are determined to be measured at the same point in time, according to positions (e.g., positions corresponding to the user's scalp) of a plurality of areas (i.e., 19 areas) in the user's scalp (e.g., rearranging the plurality of pieces of unit EEG data by classifying the plurality of pieces of unit EEG data as 11 pieces of left side data and 11 pieces of right side data (including three common channels Fz, Cz, and Pz) on the basis of the positions of a total of 19 brainwave measurement channels).

In various embodiments, the server 100 may generate a plurality of pieces of image subdata corresponding to different points in time.

In step S230, the server 100 may cumulate the rearranged plurality of pieces of unit EEG data over time. For example, the server 100 may cumulate a plurality of pieces of image subdata corresponding to different points in time and generated through step S230 over time (e.g., FIG. 6B). Each of the plurality of pieces of image subdata may include not only information on a frequency domain but also information related to channel-specific connectivity.

In step S240, the server 100 may generate QEEG data.

Figure 6A:
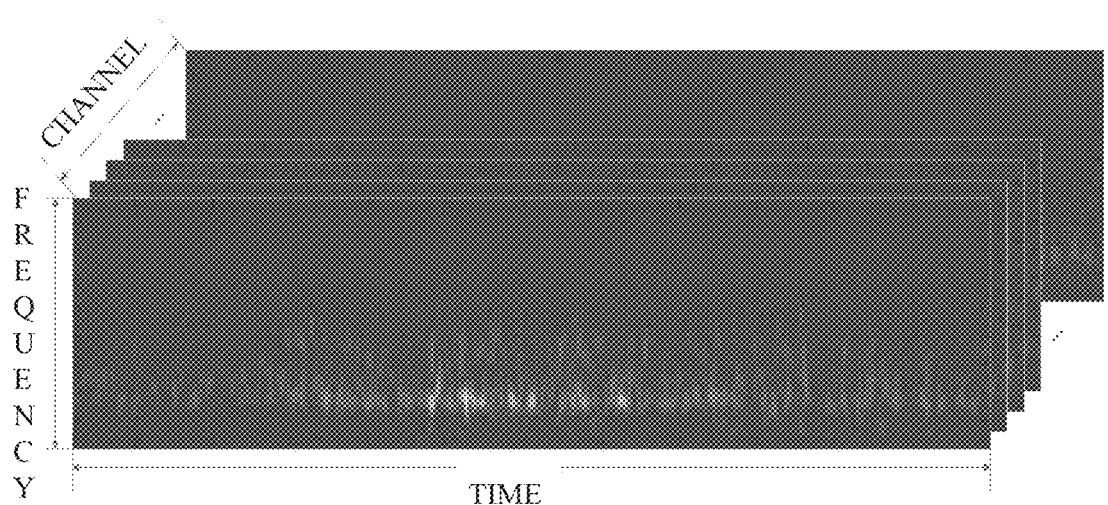
Figure 6B:
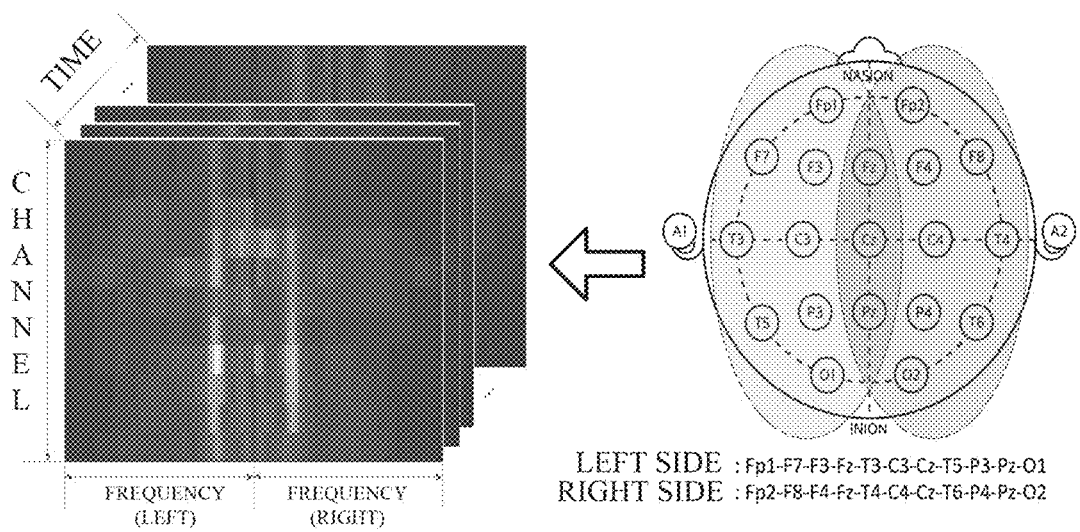
Figure 7:
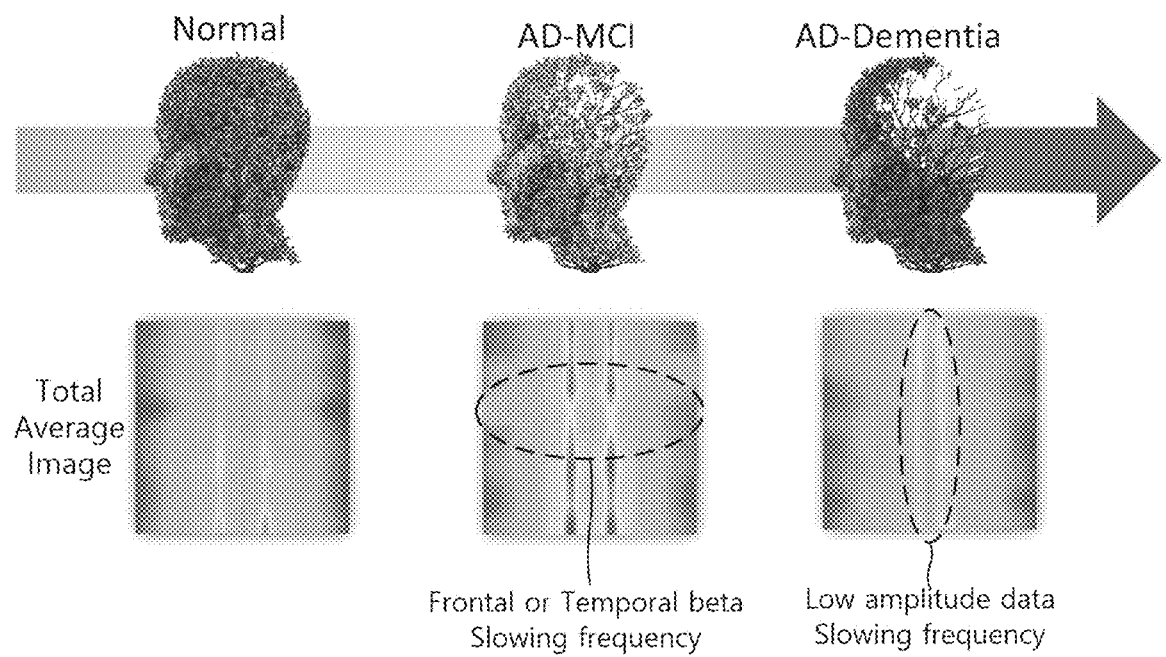
FIG. 7 is an exemplary diagram illustrating QEEG data generated in the form of a symmetrical image according to the method of generating QEEG data in various embodiments.

A frequency being used may be 1 Hz to 45 Hz, and the QEEG data may be represented in the form of a symmetrical image as shown in FIG. 6B. Since the QEEG data includes channel-specific topological information as well as topological information of all the domains, it is possible to check all information (e.g., a frequency, a frequency-specific power, a location at which a signal is generated, relation with another signal, and the pattern of a signal (regularity and complexity) time-dynamics)) at a time with only the QEEG data.

The form of QEEG data is not limited to the above-described symmetrical image, and various forms of images, such as a topology image and a time-frequency image, may be applied.

In various embodiments, the server 100 may standardize (e.g., standardization with standard scores) the QEEG data generated in step S240 on the basis of preset sex- and age-specific references. However, the standardization method is not limited thereto.

Referring back to FIGS. 3 and 4, in step S120, the server 100 may perform a first classification operation of classifying the plurality of users into a severe cognitive impairment group or a non-severe cognitive impairment group by analyzing the QEEG data.

In various embodiments, the server 100 may classify the plurality of users into the severe cognitive impairment group or the non-severe cognitive impairment group using a first classification model.

The first classification model is a model (e.g., Random forest (8:2) 5 fold cross validation (C.V)) that extracts a symmetrical image value as a feature value by performing image analysis of QEEG data in the form of a symmetrical image, calculates a probability that a corresponding user is a severe cognitive impairment patient according to the extracted feature value, and classifies the user and may be a model trained in advance using a plurality of pieces of QEEG data labeled with whether users are severe cognitive impairment patients as training data.

The first classification model includes one or more network functions, which may be formed of sets of mutually connected calculation units that may generally be called "nodes." The "nodes" may also be referred to as "neurons." The one or more network functions include one or more nodes. The nodes (or neurons) constituting the one or more network functions may be interconnected by one or more "links."

In the first classification model, one or more nodes connected through the links may relatively form the relationship between an input node and an output node. The concept of the input node is relative to the concept of the output node. An arbitrary node which is an output node for one node may be an input node for another node, and vice versa. As described above, the relationship between an input node and an output node may be established on the basis of a link. One or more output nodes may be connected to one input node through a link, and vice versa.

In the relationship between an input node and an output node connected through one link, a value of the output node may be determined on the basis of data input to the input node. Here, a node connecting the input node and the output node may have a weight. The weight may be variable, and to perform a desired function of the first classification model, the weight may be varied by a user or an algorithm. For example, when one or more input nodes are connected to one output node through links of the input nodes, the output node may determine an output node value on the basis of values input to the input nodes connected to the output node and weights set for the links each corresponding to one of the input nodes.

As described above, one or more nodes of the first classification model are interconnected through one or more links to establish the relationship between an input node and an output node in the first classification model. A characteristic of the first classification model may be determined according to the number of nodes and links in the first classification model, correlations between the nodes and the links, and a weight assigned to each of the links. For example, when two first classification models have the same number of nodes, the same number of links, and different weights between links, the two first classification models may be recognized as being different from each other.

Some of nodes constituting the first classification model may constitute one layer on the basis of distances from an initial input node. For example, a set of nodes having a distance of n from the initial input node may constitute n layer. The distance from the initial input node may be defined by the minimum number of links to be passed through to reach from the initial input node to a corresponding node. However, the definition of a layer is arbitrary for description, and the order of a layer in the first classification model may be defined in a different way than that described above. For example, a layer of nodes may be defined by a distance from a final output node.

The initial input node may be one or more nodes to which data is directly input without passing through a link in the relationship with other nodes among the nodes in the first classification model. Alternatively, the initial input node may be nodes that do not have other input nodes connected through links in the relationship between nodes on the basis of links in the first classification model network. Similarly, the final output node may be one or more nodes that do not have an output node in the relationship with other nodes among the nodes in the first classification model. Also, a hidden node may be nodes constituting the first classification model other than the initial input node or the final output node. The first classification model according to an embodiment of the present disclosure may have a form in which the number of nodes in an input layer may be larger than the number of nodes in a hidden layer and the number of nodes is reduced from the input layer to the hidden layer.

The first classification model may include one or more hidden layers. Hidden nodes in the hidden layer may use an output of a previous layer and an output of a surrounding hidden layer as inputs. In the hidden layers, the numbers of hidden nodes may be identical or different. The number of nodes in the input layer may be determined on the basis of the number of data fields of input data and may be the same as or different from the number of hidden nodes. The input data input to the input layer may be computed by the hidden nodes of the hidden layer and output by a fully connected layer (FCL) which is the output layer.

In various embodiments, the first classification model may be a deep neural network (DNN). The DNN may be a first classification model including a plurality of hidden layers in addition to an input layer and an output layer. Latent structures of data may be detected using the DNN. In other words, it is possible to detect latent structures of photos, writings, videos, voice, and music (e.g., what kinds of objects are in the photos, what the content and emotions of the writings are, and what the content and emotions of the voice are). The DNN may include a convolutional neural network (CNN), a recurrent neural network (RNN), an auto encoder, a generative adversarial network (GAN), a restricted Boltzmann machine (RBM), a deep belief network (DBN), a Q network, a U network, a Siamese network, etc. The above description of a DNN is a mere example, and the present disclosure is not limited thereto.

In various embodiments, the network functions may include an autoencoder. The autoencoder may be an artificial neural network for outputting output data similar to input data. The autoencoder may include at least one hidden layer, and an odd number of hidden layers may be disposed between an input layer and an output layer. The number of nodes in each layer may be reduced from the input layer to an intermediate layer, which is a bottleneck layer (encoding), and may expand from the bottleneck layer to the output layer (symmetrical to the input layer) symmetrically to the reduction. Nodes of a dimension reduction layer and a dimension restoration layer may be symmetrical or not.

The autoencoder may perform non-linear dimension reduction. The number of input layers and output layers may correspond to the number of sensors remaining after pre-processing of input data. In the autoencoder structure, the number of nodes in a hidden layer included in an encoder may be reduced with an increase in the distance from the input layer. When there is a very small number of nodes in the bottleneck layer (a layer having the least number of nodes between the encoder and a decoder), a sufficient amount of information may not be transmitted. Accordingly, nodes in the bottleneck layer may be maintained at a specific number or more (e.g., half or more of the number of nodes in the input layer).

In various embodiments, the first classification model may be a model trained with supervised learning. In general, supervised learning is a method of generating training data (e.g., FIG. 7) by labeling specific data and information associated with the specific data and performing training using the training data, which means a method of generating training data by labeling two pieces of data having a causal relationship and performing training with the generated training data.

More specifically, the server 100 may train the one or more network functions constituting the classification model using labeled training data. For example, the server 100 may input each piece of training input data to the one or more network functions and calculate an error by comparing each piece of output data calculated with the one or more network functions and each piece of training output data corresponding to the label of each piece of the training input data. In other words, during training of the classification model, training input data may be input to an input layer of the one or more network functions, and training output data may be compared with outputs of the one or more network functions.

The server 100 may train the classification model on the basis of errors between computation results of the one or more network functions for training input data and training output data (a label).

The server 100 may adjust weights of the one or more network functions on the basis of the errors in a backscattering manner. In other words, the server 100 may adjust the weights on the basis of errors between computation results of the one or more network functions for training input data and training output data so that outputs of the one or more network functions approach the training output data.

When training of the one or more network functions is performed for a predetermined epoch or more, the server 100 may determine whether to stop the training using verification data. The predetermined epoch may be a part of an overall training goal epoch.

The verification data may be at least a part of the labeled training data. In other words, the server 100 may train the classification model using the training data and determine whether a training effect of the classification model is a predetermined level or more using the verification data after training of the classification model is repeated for the predetermined epoch or more. For example, in the case of performing training in which a target number of repetitive training is 10 using 100 pieces of training data, the server 100 may perform repetitive training, which is the predetermined epoch, 10 times and then perform repetitive training using 10 pieces of verification data three times. When a change in the output of the classification model is the predetermined level or less during the three times of repetitive training, the server 100 may determine that further training is meaningless and terminate training.

In other words, the verification data may be used in repetitive training of the classification model to determine completion of training on the basis of whether an epoch-specific training effect is a certain level or more. The number of pieces of training data, the number of pieces of verification data, and the number of repetitions described above are mere examples, and the present disclosure is not limited thereto.

The server 100 may generate a classification model by testing performance of the one or more network functions and determining whether to activate the one or more network functions. Test data may be used to verify performance of the classification model and may be at least a part of the training data. For example, 70% of the training data may be used for training the classification model (i.e., training for adjusting weights so that a result value similar to a label is output), and 30% may be used as test data for verifying performance of the classification model. The server 100 may measure an error by inputting test data to the classification model of which training has been completed and determine whether to activate the classification model according to whether the classification model shows predetermined performance or higher.

The server 100 may verify the performance of the classification model of which training has been completed by applying the test data to the classification model of which training has been completed. When the performance of the classification model of which training has been completed is a predetermined reference or higher, the server 100 activates the classification model so that the classification model is used by another application.

Also, when the performance of the classification model of which training has been completed is less than the predetermined reference, the server 100 may deactivate and discard the classification model. For example, the server 100 may determine the performance of the generated classification model on the basis of elements such as accuracy, precision, and recall. The aforementioned references for performance evaluation are merely exemplary, and the present disclosure is not limited thereto. According to an embodiment of the present disclosure, the server 100 may generate a plurality of classification models by separately training each classification model and use only a classification model showing certain performance or higher by evaluating performance.

In various embodiments, the server 100 may calculate a severe cognitive impairment probability and non-severe cognitive impairment probability of each of the plurality of users by performing image analysis of the QEEG data using the first classification model and classify the plurality of users into a severe cognitive impairment group or a non-severe cognitive impairment group using the calculated severe cognitive impairment probabilities and non-severe cognitive impairment probabilities. For example, using the calculated severe cognitive impairment probabilities and non-severe cognitive impairment probabilities, the server 100 may classify users whose severe cognitive impairment probabilities are a preset first probability or higher and whose non-severe cognitive impairment probabilities are less than a preset second probability into the severe cognitive impairment group and classify other users who are not classified into the severe cognitive impairment group into the non-severe cognitive impairment group.

However, the classification is not limited thereto. Contrary to the above method, the server 100 may classify users whose non-severe cognitive impairment probability is a preset first probability or more and whose severe cognitive impairment probability is less than a second probability into the non-severe cognitive impairment group and other users who are not classified into the non-severe cognitive impairment group into the severe cognitive impairment group.

To subdivide users classified into the non-severe cognitive impairment group into several groups depending on severe cognitive impairment level, however, it is preferable to classify users whose severe cognitive impairment probability is the preset first probability or higher, that is, only users clearly determined to be severe cognitive impairment patients, into the severe cognitive impairment group and classify other users into the non-severe cognitive impairment group.

In various embodiments, the server 100 may filter EEG data used for training the first classification model on the basis of a preset EEG data removal condition (e.g., core clinical criteria for probable ADD).

For example, among a plurality of pieces of EEG data, the server 100 may remove EEG data determined to be abnormal on the basis of age and sex and normal EEG data of which a T-box brain protein 2 (TBR2) score is a reference or more.

Also, among the plurality of pieces of EEG data, the server 100 may remove EEG data of a case in which objective evidence is insufficient and EEG data which is atypical and questionable. However, the filtering is not limited thereto. For example, when a user satisfies the core clinical criteria for probable ADD in terms of cognitive damage but cognitive impairment suddenly develops or there is insufficient objective (medial history or cognitive test) evidence of gradual decline, the server 100 may remove the user's EEG data.

Further, the server 100 may remove, from training data, EEG data of a user who satisfies all the core clinical criteria for probable ADD but has a history of stroke temporally associated with the onset or worsening of cognitive impairment, a user with multiple cerebral infractions or a large cerebral infraction, a user with a significant level of cerebrovascular disease confirmed by severe white matter high intensity signal lesion and the like, a user with core symptoms of Lewy body dementia excluding the presence of dementia itself, and a user who uses a drug that may seriously affect an active neurological disease, a non-neurologic comorbidity, or a cognitive function.

In step S130, the server 100 may perform a second classification operation of classifying users included in the non-severe cognitive impairment group into the normal group or the aMCI group.

In various embodiments, using a second classification model, the server 100 may classify users with memory impairment among the users included in the non-severe cognitive impairment group into the aMCI group and classify users who are not classified into the aMCI group (e.g., users without memory impairment) into the normal group.

The second classification model may be, but is not limited to, a support vector machine (SVM) model, a k-nearest neighborhood (KNN) model, a tree model, or a balanced random forest (BRF) model that extracts feature values related to random forest, a light gradient boosting model (LGBM), gradient boosting, and TBR.

In various embodiments, using the second classification model, the server 100 may select and classify users with a disease related memory impairment from among the users included in the non-severe cognitive impairment group and then perform an operation of selecting and classifying normal users with no disease related to memory impairment.

To this end, the second classification model may include two or more different classification models (e.g., a classification model specialized in sensitivity and a classification model specialized in specificity) and perform a classification operation using a combination of the classification model specialized in sensitivity, the classification model specialized in specificity, and the like.

In the embodiment, the server 100 may combine the classification model specialized in sensitivity and the classification model specialized in specificity in any order and perform a classification operation using the combination of models. As an example, according to the user's selection, the server 100 may perform a classification operation through the classification model specialized in sensitivity and then perform a classification operation through the classification model specialized in specificity. As another example, according to the user's selection, the server 100 may perform a classification operation through the classification model specialized in specificity and then perform a classification operation through the classification model specialized in sensitivity.

In another embodiment, the second classification model may include at least one classification model specialized in sensitivity and at least one classification model specialized in specificity, and the server 100 may perform a classification operation using the at least one classification model specialized in sensitivity and the at least one classification model specialized in specificity. For example, the server may perform a classification operation using a classification model specialized in a first specificity, perform a classification operation using a classification model specialized in a first sensitivity, and perform a classification operation using a classification model specialized in a first specificity. Also, the server 100 may perform a classification operation using a combination of a plurality of classification models according to a purpose.

The classification model specialized in sensitivity is a model that is trained using EEG data of users with a disease related to memory impairment as first training data, that is, a model that determines that a user with a disease related to memory impairment has a disease related to memory impairment, and the classification model specialized in specificity is a model that is trained using EEG data of users with no disease related to memory impairment as second training data, that is, a model that determines that a user with no disease related to memory impairment has no disease related to memory impairment.

In various embodiments, the server 100 trains the classification model specialized in sensitivity using the first training data and trains the classification model specialized in specificity using the second training data. When there is an imbalance between the first training data and the second training data (e.g., when there is a difference of a preset value or more between the number of pieces of first training data and the number of pieces of second training data), the server 100 may make a correction so that a ratio of the first training data for training the classification model specialized in sensitivity and the second training data for training the classification model specialized in specificity becomes a certain ratio or less. In this way, it is possible to correct the imbalance in training data between the two classification models.

In step S140, the server 100 may perform a third classification operation of classifying the users included in the normal group into the WNL group or the preclinical AD group and classifying the users included in the aMCI group into the non-AD MCI group or the prodromal AD group.

First, the server 100 may generate an optimized classification model for user classification. For example, the server 100 may generate a third classification model for classifying the users included in the normal group into the WNL group or the preclinical AD group and a fourth classification model for classifying the users included in the aMCI group into the non-AD MCI group or the prodromal AD group. An optimized classification model generation method performed by the server 100 will be described below with reference to FIGS. 8 and 9.

Figure 8:
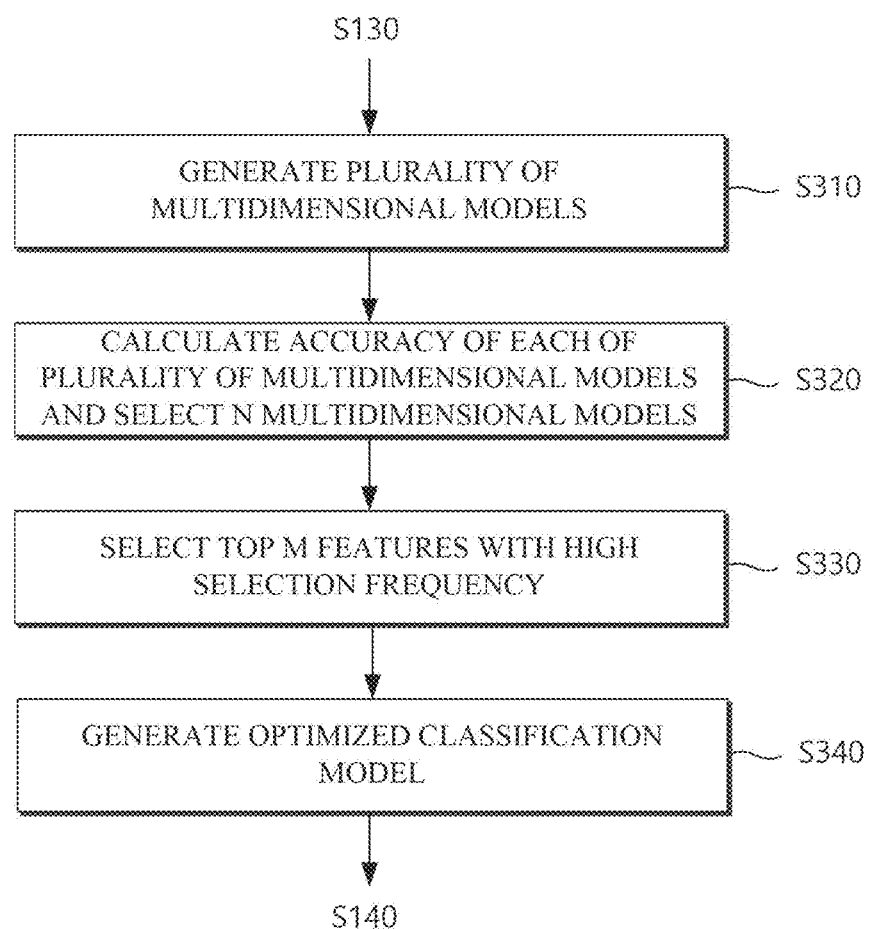
FIG. 8 is a flowchart illustrating a method of generating an optimized classification model in various embodiments.
Figure 9:
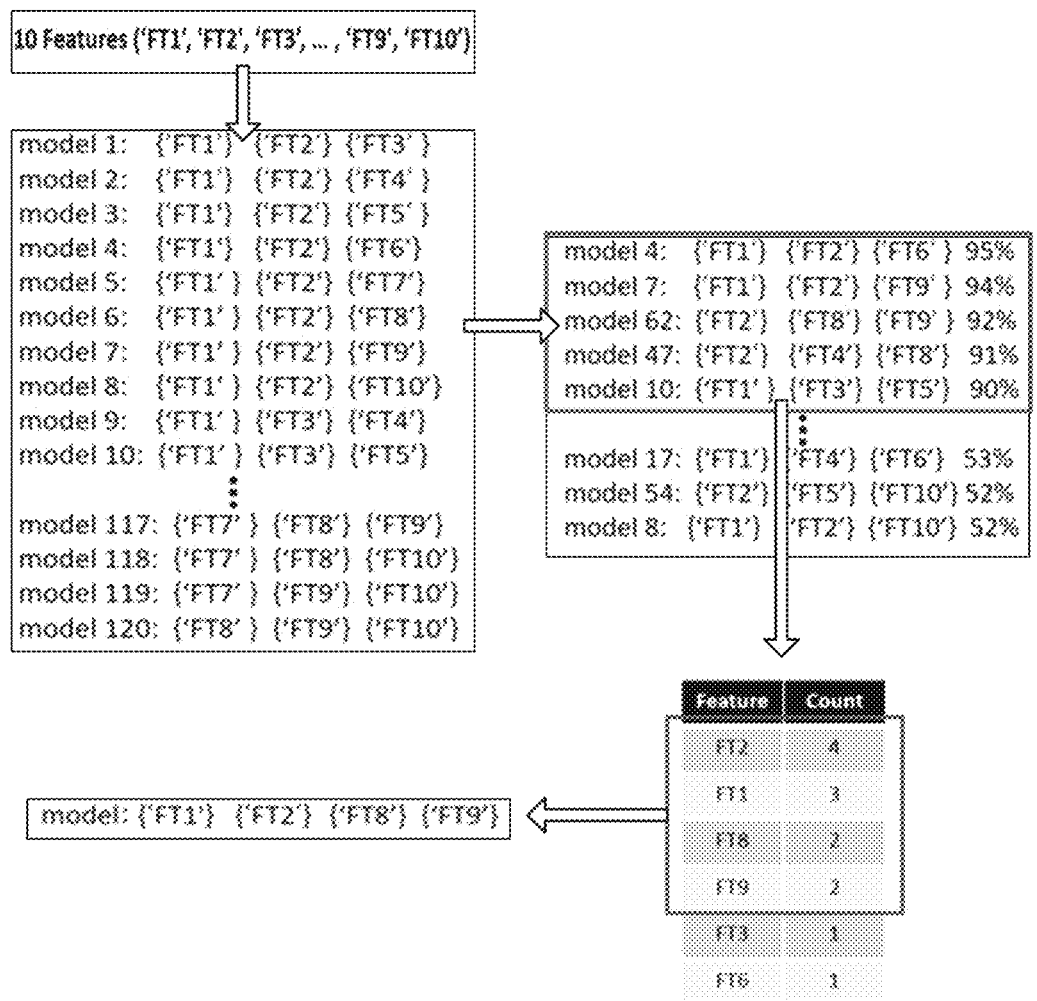
FIG. 9 is a diagram illustrating a process of generating an optimized classification model according to the method of FIG. 8 in various embodiments.

FIG. 8 is a flowchart illustrating a method of generating an optimized classification model in various embodiments, and FIG. 9 is a diagram illustrating a process of generating an optimized classification model according to the method of FIG. 8 in various embodiments.

Referring to FIGS. 8 and 9, in step S310, the server 100 may generate a plurality of multidimensional models including different feature value combinations. For example, the server 100 may generate a plurality of different feature value combinations by randomly and repeatedly selecting three, which is a preset number, of ten feature values (e.g., among "FT1," "FT1," . . . , and "FT10" of FIG. 9) and generate a plurality of multidimensional models (three-dimension (3D) models) using each of the generated plurality of feature value combinations. In this case, the server 100 may generate multidimensional models for all the different feature value combinations of the 10 feature values (e.g., $_{10}C_3$ combinations).

Feature values constituting the multidimensional models may be derived by analyzing the plurality of pieces of EEG data each collected from the plurality of users but are not limited thereto.

In step S320, the server 100 may calculate the accuracy of each of the plurality of multidimensional models generated in step S310. For example, the server 100 may classify the plurality of users using the plurality of multidimensional models according to a preset condition and calculate the accuracy of classification by comparing the classification results and actual results.

To separately generate a third classification model for classifying the users of the normal group and a fourth classification model for classifying the users of the aMCI group, the server 100 may separately calculate the accuracies of classification according to different conditions. For example, to generate a third classification model, the server 100 may classify the users included in the normal group into the WNL group or the preclinical AD group using the plurality of multidimensional models and calculate the accuracies of classification in the normal group by comparing the classification results and the actual results. Also, to generate a fourth classification model, the server 100 may classify the users included in the aMCI group into the non-AD MCI group or the prodromal AD group using the plurality of multidimensional models and calculate the accuracies of classification in the aMCI group by comparing the classification results and the actual results again.

The actual results may be results of directly classifying the plurality of users according to various tests (e.g., a verbal fluency test, a Boston naming test, a mini mental state examination, a word list memory test, a constructional behavior test, a word list recall test, a word list recognition test, a constructional recall test, and a path making test A/B) conducted on the plurality of users.

The accuracies may represent, in numbers, the degree of similarity between the classification results based on the plurality of multidimensional models and the actual results but is not limited thereto.

In step S330, the server 100 may select top N multidimensional models in decreasing order of accuracy calculated in step S320, count the number of each of feature values included in each of the N multidimensional models, and select M feature values in decreasing order of count value.

For example, as shown in FIG. 9, the server 100 may arrange the plurality of multidimensional models in decreasing order of accuracy calculated in step S320 and select the top five of the arranged plurality of multidimensional models. Subsequently, the server 100 may select top M feature values from among feature values included in the top five multidimensional models.

In this case, to generate a classification model with higher accuracy than the plurality of multidimensional models, the server 100 may include, in a classification model to be generated, a greater number of feature values than feature values included in the plurality of multidimensional models. For example, when the plurality of multidimensional models are 3D models including three feature values, top four feature values may be selected so that an optimized classification model includes four or more feature values.

In step S340, the server 100 may generate an optimized classification model including the M feature values selected in step S330.

Referring back to FIGS. 3 and 4, using the third classification model, the server 100 may classify users without subjective cognitive decline (SCD) among the users included in the normal group into the WNL group and classify users with SCD into the preclinical AD group.

Also, using the fourth classification model, the server 100 may classify users with retrieval failure among the users included in the aMCI group into the non-AD MCI group and classify users with encoding failure into the prodromal AD group.

In step S150, the server 100 may score severe cognitive impairment levels of users included in each of the WNL group, the preclinical AD group, the non-AD MCI group, the prodromal AD group, and the severe cognitive impairment group using the results of classifying the plurality of users through steps S120 to S140.

The severe cognitive impairment level may be the degree of a factor that is a criterion for classifying each group. For example, severe cognitive impairment levels of the users included in the normal group may be the degree of SCD, severe cognitive impairment levels of the users included in the non-AD MCI group in the aMCI group may be the degrees of retrieval failure, and severe cognitive impairment levels of the users included in the prodromal AD group may be the degrees of encoding failure. Also, severe cognitive impairment levels of the users included in the severe cognitive impairment group may be the degrees of actual progression of severe cognitive impairment. However, severe cognitive impairment levels are not limited thereto.

In various embodiments, the server 100 may score users belong to each of the WNL group, the preclinical AD group, the non-AD MCI group, the prodromal AD group, and the severe cognitive impairment group using a scoring model.

The scoring model may be a model for calculating a corresponding user's probability of dementia as a score using information (e.g., information on the group to which the users belong and severe cognitive impairment levels) on users belonging to a group as inputs. For example, the scoring model may generate a scoring function for scoring users belonging to each of the preclinical AD group, the non-AD MCI group, the prodromal AD group, and the severe cognitive impairment group and calculate a score of a user by inputting the foregoing input values to the generated scoring function.

Figure 10:
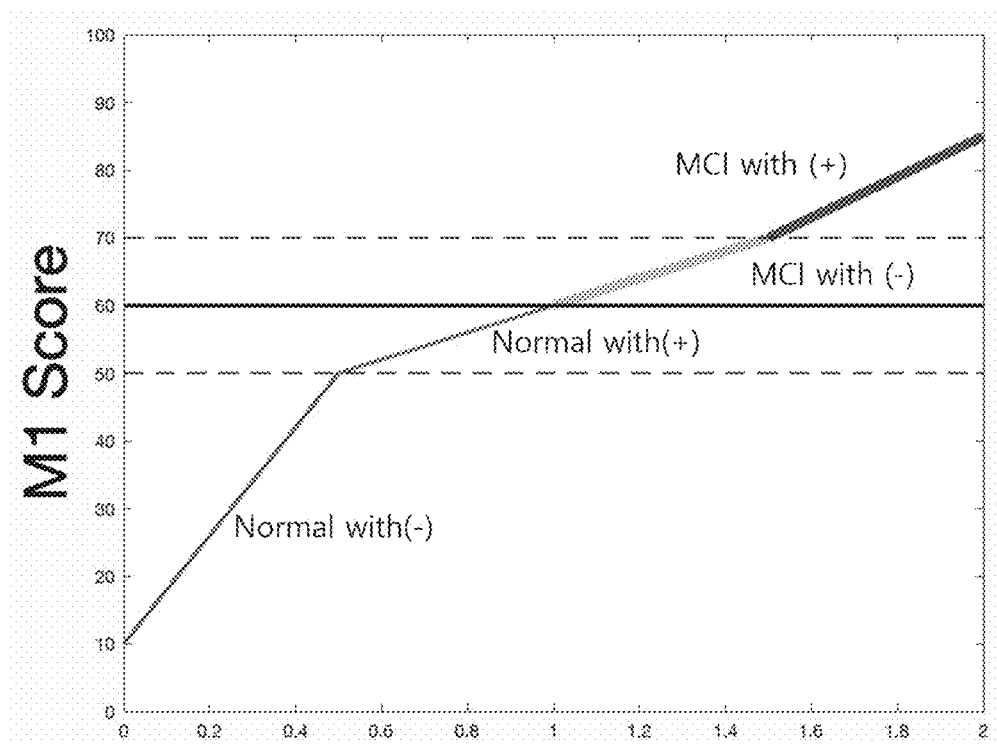
FIG. 10 is a graph illustrating a process of scoring severe cognitive impairment levels of users included in each group in various embodiments.

As shown in FIG. 10, the scoring function may be implemented in the form of first-order functions with different slopes depending on a group but is not limited thereto.

In various embodiments, on the basis of the scoring function shown in FIG. 10, the server 100 may give scores of 0 to 50 to users included in the WNL group and give scores of 50 to 60 to users included in the preclinical AD group depending on severe cognitive impairment level.

Also, on the basis of the scoring function shown in FIG. 10, the server 100 may give scores of 60 to 70 to users included in the non-AD MCI group, give scores of 70 to 85 to users included in the prodromal AD group, and give scores of 85 to 100 to users included in the severe cognitive impairment group depending on severe cognitive impairment level.

Figure 11:
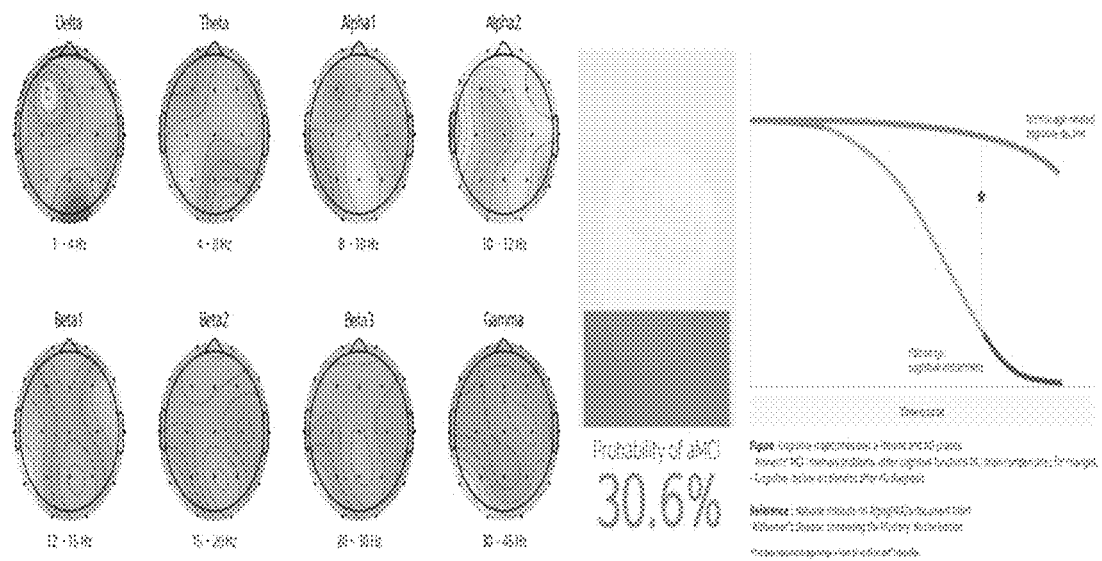
FIGS. 11 and 12 are exemplary diagrams illustrating result data obtained according to the method of classifying severe cognitive impairment patients by analyzing EEG data in various embodiments.
Figure 11:
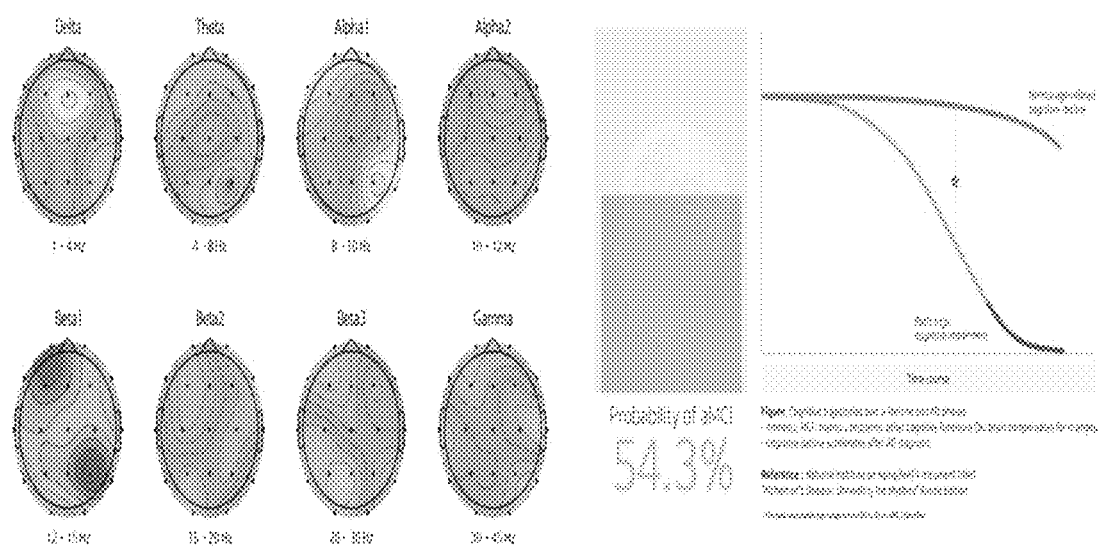
Figure 12:
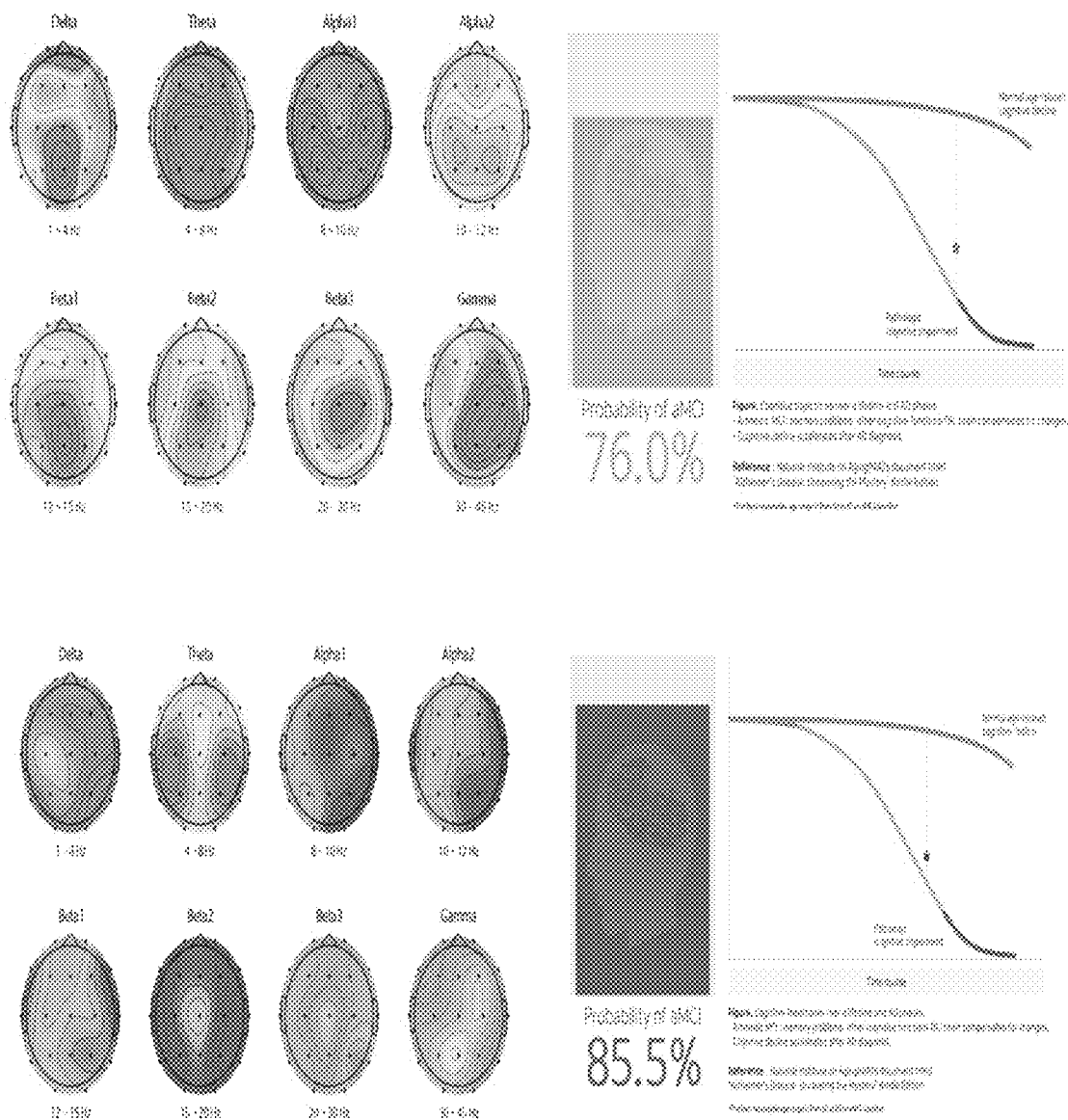

In various embodiments, when a dementia diagnosis request including EEG data is received from a first user, the server 100 may perform an operation of generating QEEG data of the first user using the EEG data of the first user in response to the dementia diagnosis request, an operation of classifying the first user into any one group by analyzing the QEEG data, and an operation of scoring the user according to the classified group and a severe cognitive impairment level and may combine results of performing the operations and provide a result report (e.g., FIGS. 11 and 12).

In this way, it is possible to determine whether a user is a severe cognitive impairment patient by a simple operation of collecting and inputting the user's EEG data, and even when the user is not a severe cognitive impairment patient, the possibility that the user will be a severe cognitive impairment patient is provided in a number so that the user can clearly understand his or her status in relation to severe cognitive impairment and take measures accordingly.

The above method of classifying severe cognitive impairment patients by analyzing EEG data has been described with reference to the flowcharts shown in the drawings. For convenience of description, the method of classifying severe cognitive impairment patients by analyzing EEG data has been shown and described as a series of blocks, but the present disclosure is not limited to the order of blocks. Some blocks may be performed in a different order than that shown and performed herein or may be performed simultaneously. Also, the method of classifying severe cognitive impairment patients by analyzing EEG data may be performed with a new block not described in this specification and drawings added or some blocks omitted or changed.

According to various embodiments of the present disclosure, a plurality of users are classified into users in a normal state and patients with dementia by analyzing electroencephalogram (EEG) data of the plurality of users, and also the users' probabilities of dementia the in the normal state are subdivided in consideration of whether the users have memory impairment, the types and degrees of memory impairment, and the like. Accordingly, it is possible to not only identify patients currently suffering from dementia but also screen users who may develop dementia in the early stage among the users in the normal state.

Effects of the present disclosure are not limited to those described above, and other effects which have not been described will be clearly understood by those of ordinary skill in the art from the following descriptions.

Although embodiments of the present disclosure have been described above with reference to the accompanying drawings, those of ordinary skill in the art should appreciate that the present disclosure can be implemented in other specific forms without changing the technical spirit or essential characteristics thereof. Therefore, the above-described embodiments should be construed as exemplary in all aspects and not limiting.

What is claimed is:

1. A method for determining patients with severe cognitive impairment, the method comprising:
    receiving, from a plurality of user terminals and using at least one of one or more computing devices over a communication network, requests for evaluating probability and classification of severe cognitive impairment of a plurality of users, respectively, wherein each of the plurality of user terminals is configured to provide a user interface to allow each of the plurality of users to input the request and is connected to a brainwave measurement device worn by the user;
    in response to the request, collecting, using at least one of the one or more computing devices, electroencephalogram (EEG) data on the plurality of users by, for each of the plurality of users:
        operating a plurality of brainwave measurement channels that are provided at the brainwave measurement device and disposed at a plurality of positions at each user's head to receive independent brainwave signals separately measured through the channels, and collecting, based on the operation of the plurality of brainwave measurement channels, a plurality of pieces of unit EEG data that represent the independent brainwave signals,
        generating quantitative EEG (QEEG) data by (i) quantifying the plurality of collected pieces of unit EEG data and (ii) converting the plurality of quantified pieces of unit EEG data into images, and
        standardizing the generated QEEG data based on a preset sex-specific reference and an age-specific reference;
    analyzing, using at least one of the one or more computing devices, the collected EEG data to classify the plurality of users into a severe cognitive impairment group or a non-severe cognitive impairment group;
    classifying, using at least one of the one or more computing devices, users included in the non-severe cognitive impairment group into a normal group or an amnestic mild cognitive impairment (aMCI) group;
    classifying, using at least one of the one or more computing devices, users included in the normal group into a within normal limits (WNL) group or a preclinical Alzheimer's disease (AD) group; and
    classifying, using at least one of the one or more computing devices, users included in the aMCI group into a non-AD MCI group or a prodromal AD group,
    wherein generating the QEEG data comprises:
        calculating, using at least one of the one or more computing devices, frequency domains for the plurality of pieces of unit EEG data based on fast-Fourier transform,
        rearranging, based on the calculated frequency domains and using at least one of the one or more computing devices, subset frequency domains of the calculated frequency domains based on the positions of the plurality of brainwave measurement channels, the subset frequency domains corresponding to subset pieces of unit EEG data that are measured simultaneously among the plurality of pieces of unit EEG data, and
        generating, based on the rearranged subset frequency domains and using at least one of the one or more computing devices, the QEEG data in a form of a symmetrical image by accumulating the rearranged subset pieces of unit EEG data over time,
    wherein the method further comprises:
        transmitting, based on the requests of the plurality of user terminals and using at least one of the one or more computing devices to the plurality of user terminals, results of classifying the plurality of users into at least one of the severe cognitive impairment group, the non-severe cognitive impairment group, the normal group, the aMCI group, the WNL group, the preclinical AD group, the non-AD MCI group, or the prodromal AD group such that the plurality of user terminals output the results using the user interfaces, respectively.

2. The method of claim 1, wherein analyzing the collected EEG data further comprises:
    performing, using at least one of the one or more computing devices, image analysis of the generated QEEG data using a first classification model;
    calculating, using at least one of the one or more computing devices and based on the image analysis, a severe cognitive impairment probability and a non-severe cognitive impairment probability of each of the plurality of users; and
    classifying, using at least one of the one or more computing devices and based on the calculated severe cognitive impairment probabilities and the calculated non-severe cognitive impairment probabilities, the plurality of users into the severe cognitive impairment group or the non-severe cognitive impairment group.

3. The method of claim 1, wherein classifying the users included in the non-severe cognitive impairment group into the normal group or the aMCI group, comprises:
    classifying first users with memory impairment into the aMCI group, the first users being selected from the users included in the non-severe cognitive impairment group; and
    classifying second users into the normal group based on a second classification model, the second users being not classified into the aMCI group.

4. The method of claim 1, wherein classifying the users included in the normal group into the WNL group or the preclinical AD group, comprises:

generating an optimized classification model for user classification, the optimized classification model including a third classification model and a fourth classification model;

classifying third users without subjective cognitive decline (SCD) into the WNL group, the third user being selected from the users included in the normal group;

classifying fourth users with SCD into the preclinical AD group based on the third classification model;

classifying fifth users with retrieval failure into the non-AD MCI group, the fifth users being selected from the users included in the aMCI group; and classifying sixth users with encoding failure into the prodromal AD group based on the fourth classification model.

5. The method of claim 4, wherein generating the optimized classification model comprises:
generating a plurality of multidimensional models by:
deriving a plurality of feature values by analyzing the plurality of pieces of EEG data collected from each of the plurality of users,
randomly and repeatedly selecting a preset number of feature values from the plurality of feature values,
generating, based on the selection of the preset number of feature values, a plurality of feature value combinations, and
generating the plurality of multidimensional models based on each of the plurality of feature value combinations;
calculating an accuracy of each of the plurality of multidimensional models;
selecting N multidimensional models in decreasing order of accuracy;
counting a number of feature values included in each of the selected N multidimensional models;
selecting M feature values in decreasing order of count value; and
generating the optimized classification model including the selected M feature values.

6. The method of claim 1, further comprising:
scoring, based on (i) classifying the plurality of users into the severe cognitive impairment group or the non-severe cognitive impairment group, (ii) classifying the users included in the non-severe cognitive impairment group into the normal group or the aMCI group, and (iii) classifying the users included in the normal group into the WNL group or the preclinical AD group, severe cognitive impairment levels of users included in each of the WNL group, the preclinical AD group, the non-AD MCI group, the prodromal AD group, and the severe cognitive impairment group.

7. The method of claim 6, wherein scoring the severe cognitive impairment levels of the users comprises:
scoring 0 to 50 to the users included in the WNL group based on the severe cognitive impairment levels;
scoring 50 to 60 to the users included in the preclinical AD group based on the severe cognitive impairment levels;
scoring 60 to 70 to the users included in the non-AD MCI group based on the severe cognitive impairment levels;
scoring 70 to 85 to the users included in the prodromal AD group based on the severe cognitive impairment levels; and
scoring 85 to 100 to the users included in the severe cognitive impairment group based on the severe cognitive impairment levels.

8. A server for classifying severe cognitive impairment patients by analyzing electroencephalogram (EEG) data, the server comprising:
a processor; and
a memory storing instructions that, when executed by the processor, cause the server to perform operations comprising:
receiving, from a plurality of user terminals over a communication network, requests for evaluating probability and classification of severe cognitive impairment of a plurality of users, respectively, wherein each of the plurality of user terminals is configured to provide a user interface to allow each of the plurality of users to input the request and is connected to a brainwave measurement device worn by the user;
in response to the request, collecting electroencephalogram (EEG) data on the plurality of users by, for each of the plurality of users:
operating a plurality of brainwave measurement channels that are provided at the brainwave measurement device and disposed at a plurality of positions at each user's head to receive independent brainwave signals separately measured through the channels, and collecting, based on the operation of the plurality of brainwave measurement channels, a plurality of pieces of unit EEG data that represent the independent brainwave sign,
generating quantitative EEG (QEEG) data by quantifying the plurality of collected pieces of unit EEG data and converting the plurality of quantified pieces of unit EEG data into images, and
standardizing the generated QEEG data based on a preset sex-specific reference and an age-specific reference;
analyzing the collected EEG data to classify the plurality of users into a severe cognitive impairment group or a non-severe cognitive impairment group;
classifying users included in the non-severe cognitive impairment group into a normal group or an amnestic mild cognitive impairment (aMCI) group;
classifying users included in the normal group into a within normal limits (WNL) group or a preclinical Alzheimer's disease (AD) group; and
classifying users included in the aMCI group into a non-AD MCI group or a prodromal AD group,
wherein generating the QEEG data comprises:
calculating frequency domains for the plurality of pieces of unit EEG data based on fast-Fourier transform,
rearranging, based on the calculated frequency domains, subset frequency domains of the calculated frequency domains based on the positions of the plurality of brainwave measurement channels, the subset frequency domains corresponding to subset pieces of unit EEG data that are measured simultaneously among the plurality of pieces of unit EEG data, and
generating, based on the rearranged subset frequency domains, the QEEG data in a form of a symmetrical image by accumulating the rearranged subset pieces of unit EEG data over time,
wherein the operations further comprise:
transmitting, based on the requests of the plurality of user terminals and to the plurality of user terminals, results of classifying the plurality of users into at least one of the severe cognitive impairment group, the non-severe cognitive impairment group, the normal group, the aMCI group, the WNL group, the preclinical AD group, the non-AD MCI group, or the prodromal AD group such that the plurality of user terminals output the results using the user interfaces, respectively.

9. The server of claim 8, wherein analyzing the collected EEG data further comprises:
performing, using at least one of the one or more computing devices, image analysis of the generated QEEG data using a first classification model;
calculating, using at least one of the one or more computing devices and based on the image analysis, a severe cognitive impairment probability and a non-severe cognitive impairment probability of each of the plurality of users; and
classifying, using at least one of the one or more computing devices and based on the calculated severe cognitive impairment probabilities and the calculated non-severe cognitive impairment probabilities, the plurality of users into the severe cognitive impairment group or the non-severe cognitive impairment group.

10. The server of claim 8, wherein classifying the users included in the non-severe cognitive impairment group into the normal group or the aMCI group, comprises:
classifying first users with memory impairment into the aMCI group, the first users being selected from the users included in the non-severe cognitive impairment group; and
classifying second users into the normal group based on a second classification model, the second users being not classified into the aMCI group.

11. The server of claim 8, wherein classifying the users included in the normal group into the WNL group or the preclinical AD group, comprises:
generating an optimized classification model for user classification, the optimized classification model including a third classification model and a fourth classification model;
classifying third users without subjective cognitive decline (SCD) into the WNL group, the third user being selected from the users included in the normal group;
classifying fourth users with SCD into the preclinical AD group based on the third classification model;
classifying fifth users with retrieval failure into the non-AD MCI group, the fifth users being selected from the users included in the aMCI group; and
classifying sixth users with encoding failure into the prodromal AD group based on the fourth classification model.

12. The server of claim 11, wherein generating the optimized classification model comprises:
generating a plurality of multidimensional models by:
deriving a plurality of feature values by analyzing the plurality of pieces of EEG data collected from each of the plurality of users,
randomly and repeatedly selecting a preset number of feature values from the plurality of feature values,
generating, based on the selection of the preset number of feature values, a plurality of feature value combinations, and
generating the plurality of multidimensional models based on each of the plurality of feature value combinations;
calculating an accuracy of each of the plurality of multidimensional models;
selecting N multidimensional models in decreasing order of accuracy;
counting a number of feature values included in each of the selected N multidimensional models;
selecting M feature values in decreasing order of count value; and
generating the optimized classification model including the selected M feature values.

13. The server of claim 8, wherein the operations further comprise:
scoring, based on (i) classifying the plurality of users into the severe cognitive impairment group or the non-severe cognitive impairment group, (ii) classifying the users included in the non-severe cognitive impairment group into the normal group or the aMCI group, and (iii) classifying the users included in the normal group into the WNL group or the preclinical AD group, severe cognitive impairment levels of users included in each of the WNL group, the preclinical AD group, the non-AD MCI group, the prodromal AD group, and the severe cognitive impairment group.

14. The server of claim 13, wherein scoring the severe cognitive impairment levels of the users comprises:
scoring 0 to 50 to the users included in the WNL group based on the severe cognitive impairment levels;
scoring 50 to 60 to the users included in the preclinical AD group based on the severe cognitive impairment levels;
scoring 60 to 70 to the users included in the non-AD MCI group based on the severe cognitive impairment levels;
scoring 70 to 85 to the users included in the prodromal AD group based on the severe cognitive impairment levels; and
scoring 85 to 100 to the users included in the severe cognitive impairment group based on the severe cognitive impairment levels.

15. A non-transitory computer-readable medium having stored therein a computer program for causing a computing device to execute operations comprising:
receiving, from a plurality of user terminals over a communication network, requests for evaluating probability and classification of severe cognitive impairment of a plurality of users, respectively, wherein each of the plurality of user terminals is configured to provide a user interface to allow each of the plurality of users to input the request and is connected to a brainwave measurement device worn by the user;
collecting electroencephalogram (EEG) data on the plurality of users by, for each of the plurality of users:
operating a plurality of brainwave measurement channels that are provided at the brainwave measurement device and disposed at a plurality of positions at each user's head to receive independent brainwave signals separately measured through the channels, and collecting, based on the operation of the plurality of brainwave measurement channels, a plurality of pieces of unit EEG data that represent the independent brainwave signals;
generating quantitative EEG (QEEG) data by quantifying the plurality of collected pieces of unit EEG data and converting the plurality of quantified pieces of unit EEG data into images, and
standardizing the generated QEEG data based on a preset sex-specific reference and an age-specific reference;

analyzing the collected EEG data to classify the plurality of users into a severe cognitive impairment group or a non-severe cognitive impairment group;

classifying users included in the non-severe cognitive impairment group into a normal group or an amnestic mild cognitive impairment (aMCI) group;

classifying users included in the normal group into a within normal limits (WNL) group or a preclinical Alzheimer's disease (AD) group; and classifying users included in the aMCI group into a non-AD MCI group or a prodromal AD group, wherein generating the QEEG data comprises:
  calculating frequency domains for the plurality of pieces of unit EEG data based on fast-Fourier transform,
  rearranging, based on the calculated frequency domains, subset frequency domains of the calculated frequency domains based on the positions of the plurality of brainwave measurement channels, the subset frequency domains corresponding to subset pieces of unit EEG data that are measured simultaneously among the plurality of pieces of unit EEG data, and
  generating, based on the rearranged subset frequency domains, the QEEG data in a form of a symmetrical image by accumulating the rearranged subset pieces of unit EEG data over time,
wherein the operations further comprise:
  transmitting, based on the requests of the plurality of user terminals and to the plurality of user terminals, results of classifying the plurality of users into at least one of the severe cognitive impairment group, the non-severe cognitive impairment group, the normal group, the aMCI group, the WNL group, the preclinical AD group, the non-AD MCI group, or the prodromal AD group such that the plurality of user terminals output the results using the user interfaces, respectively.

16. The non-transitory computer-readable medium of claim 15, wherein analyzing the collected EEG data further comprises:
  performing, using at least one of the one or more computing devices, image analysis of the generated QEEG data using a first classification model;
  calculating, using at least one of the one or more computing devices and based on the image analysis, a severe cognitive impairment probability and a non-severe cognitive impairment probability of each of the plurality of users; and
  classifying, using at least one of the one or more computing devices and based on the calculated severe cognitive impairment probabilities and the calculated non-severe cognitive impairment probabilities, the plurality of users into the severe cognitive impairment group or the non-severe cognitive impairment group.

17. The non-transitory computer-readable medium of claim 15, wherein classifying the users included in the non-severe cognitive impairment group into the normal group or the aMCI group, comprises:
  classifying first users with memory impairment into the aMCI group, the first users being selected from the users included in the non-severe cognitive impairment group; and
  classifying second users into the normal group based on a second classification model, the second users being not classified into the aMCI group.

18. The non-transitory computer-readable medium of claim 15, wherein classifying the users included in the normal group into the WNL group or the preclinical AD group, comprises:
  generating an optimized classification model for user classification, the optimized classification model including a third classification model and a fourth classification model;
  classifying third users without subjective cognitive decline (SCD) into the WNL group, the third user being selected from the users included in the normal group;
  classifying fourth users with SCD into the preclinical AD group based on the third classification model;
  classifying fifth users with retrieval failure into the non-AD MCI group, the fifth users being selected from the users included in the aMCI group; and
  classifying sixth users with encoding failure into the prodromal AD group based on the fourth classification model.

19. The non-transitory computer-readable medium of claim 18, wherein generating the optimized classification model comprises:
  generating a plurality of multidimensional models by:
    deriving a plurality of feature values by analyzing the plurality of pieces of EEG data collected from each of the plurality of users,
    randomly and repeatedly selecting a preset number of feature values from the plurality of feature values,
    generating, based on the selection of the preset number of feature values, a plurality of feature value combinations, and
    generating the plurality of multidimensional models based on each of the plurality of feature value combinations;
  calculating an accuracy of each of the plurality of multidimensional models;
  selecting N multidimensional models in decreasing order of accuracy;
  counting a number of feature values included in each of the selected N multidimensional models;
  selecting M feature values in decreasing order of count value; and
  generating the optimized classification model including the selected M feature values.

20. The non-transitory computer-readable medium of claim 15, wherein the operations further comprise:
  scoring, based on (i) classifying the plurality of users into the severe cognitive impairment group or the non-severe cognitive impairment group, (ii) classifying the users included in the non-severe cognitive impairment group into the normal group or the aMCI group, and (iii) classifying the users included in the normal group into the WNL group or the preclinical AD group, severe cognitive impairment levels of users included in each of the WNL group, the preclinical AD group, the non-AD MCI group, the prodromal AD group, and the severe cognitive impairment group.

* * * * *